(12) United States Patent
Bouchard

(10) Patent No.: US 12,295,756 B2
(45) Date of Patent: May 13, 2025

(54) SUPPORT SYSTEMS FOR SUPPORTING EQUIPMENT

(71) Applicant: TECHNOLOGIES CGC INC., Quebec (CA)

(72) Inventor: Carl Bouchard, Quebec (CA)

(73) Assignee: TECHNOLOGIES CGC INC., Quebec (CA)

( * ) Notice: Subject to any disclaimer, the term of this patent is extended or adjusted under 35 U.S.C. 154(b) by 166 days.

(21) Appl. No.: 17/927,215

(22) PCT Filed: May 25, 2021

(86) PCT No.: PCT/CA2021/050706
§ 371 (c)(1),
(2) Date: Nov. 22, 2022

(87) PCT Pub. No.: WO2021/237347
PCT Pub. Date: Dec. 2, 2021

(65) Prior Publication Data
US 2023/0200925 A1    Jun. 29, 2023

Related U.S. Application Data

(60) Provisional application No. 63/029,648, filed on May 25, 2020.

(51) Int. Cl.
*A61B 50/26* (2016.01)
*A61B 50/22* (2016.01)

(52) U.S. Cl.
CPC .............. *A61B 50/26* (2016.02); *A61B 50/22* (2016.02)

(58) Field of Classification Search
CPC .............. A61M 5/1415; A61M 5/1413; A61M 2209/086; A61B 50/22; A61B 50/26
See application file for complete search history.

(56) References Cited

U.S. PATENT DOCUMENTS

| 4,511,158 A | 4/1985 | Varga et al. |
| 5,152,486 A | 10/1992 | Kabanek et al. |

(Continued)

FOREIGN PATENT DOCUMENTS

| DE | 102017110001 A1 | 11/2018 |
| EP | 2800545 B1 | 7/2016 |

(Continued)

OTHER PUBLICATIONS

International Search Report and Written opinion issued in corresponding International application No. PCT/CA2021/050706 on Aug. 5, 2021.

(Continued)

*Primary Examiner* — Bradley Duckworth
(74) *Attorney, Agent, or Firm* — BCF LLP

(57) ABSTRACT

Support system for supporting equipment comprising: a back support; shelves spaced from one another and extending from the back support and arranged to support the equipment, each shelf comprising: a connecting mechanism for providing a connected position in which the equipment is connected to the given shelf such that separation of the given shelf and the equipment along a first axis is blocked but relative movement along a second axis is possible; a locking mechanism for providing a locked position in which relative movement of the equipment and the given shelf along the second axis is blocked; and a release mechanism for releasing the locked position to permit the relative movement along the second axis, the release mechanism including an actuator on the given shelf or the equipment which can be actuated by a user.

20 Claims, 18 Drawing Sheets

(56) References Cited

U.S. PATENT DOCUMENTS

| | | | |
|---|---|---|---|
| 5,362,021 A | 11/1994 | Phillips | |
| 7,884,735 B2 * | 2/2011 | Newkirk | A61G 7/012 |
| | | | 5/512 |
| 8,196,939 B2 * | 6/2012 | Bustle | A47B 21/0314 |
| | | | 280/47.35 |
| 9,746,125 B2 | 8/2017 | Bowman | |
| 9,789,247 B2 | 10/2017 | Kamen et al. | |
| 9,808,316 B2 | 11/2017 | Hasegawa | |
| 11,007,951 B1 | 5/2021 | Zarecky | |
| 11,129,933 B2 * | 9/2021 | Kamen | G16H 70/40 |
| 11,353,155 B2 * | 6/2022 | Bouchard | F16M 11/041 |
| 11,725,770 B2 * | 8/2023 | Bouchard | F16B 5/0657 |
| | | | 248/637 |
| 2002/0011543 A1 | 1/2002 | Chinn et al. | |
| 2003/0046764 A1 | 3/2003 | Smeed | |
| 2008/0217910 A1 | 9/2008 | Walke | |
| 2012/0211446 A1 * | 8/2012 | Cote | A61B 50/15 |
| | | | 211/85.13 |
| 2012/0262039 A1 | 10/2012 | Daugbjerg et al. | |
| 2014/0374564 A1 | 12/2014 | Schroeder et al. | |
| 2014/0374565 A1 | 12/2014 | Tan | |
| 2015/0041419 A1 | 2/2015 | Hasegawa | |
| 2015/0090849 A1 | 4/2015 | Breitweiser et al. | |
| 2015/0273138 A1 | 10/2015 | Wolff et al. | |
| 2016/0031382 A1 | 2/2016 | Chinn et al. | |
| 2016/0324701 A1 | 11/2016 | Cambridge et al. | |
| 2017/0209318 A1 | 7/2017 | Schroeder et al. | |

FOREIGN PATENT DOCUMENTS

| | | |
|---|---|---|
| EP | 2916887 B1 | 9/2016 |
| EP | 2697462 B1 | 6/2019 |

OTHER PUBLICATIONS

Supplementary European Search Report issued in co-pending European patent application No. 21814330.3 on May 17, 2024.

\* cited by examiner

SUPPORT SYSTEMS FOR SUPPORTING EQUIPMENT

CROSS-REFERENCE TO RELATED APPLICATIONS

This application is a National Phase Entry of international PCT patent application No. PCT/CA2021/050706 filed on May 25, 2021, which claims the benefit of priority of U.S. Provisional Patent Application No. 63/029,648 filed on May 25, 2020. The contents of the above-noted applications are incorporated herein by reference.

TECHNICAL FIELD

The present technology relates to support systems for supporting equipment, and more specifically, although not exclusively, to support systems for supporting equipment, such as medical equipment, in a stacked configuration.

BACKGROUND

In certain situations, such as during provision of medical care, there can arise a need to connect a number of pieces of equipment to a patient or to each other. One example of such equipment is medical equipment such as infusion pumps.

With existing stackable systems, the individual items are stacked by connecting them together. However, independent removal or installation of an individual item of equipment is not possible with this configuration and requires separation of all individual items from each other. It will be appreciated that this can unnecessarily slow down installation and/or removal of equipment which in medical situations in particular, can be critical and potentially life-threatening.

During transportation of the equipment, there are further considerations. For example, in the case of medical equipment that accompanies a patient, each item of equipment must be secured during transportation to prevent injuries as well as damage to the equipment.

Current solutions, particularly with stackable systems, are far from ideal. They do not secure the medical equipment in a manner which allows for secure restraint as well as quick and easy release of each item of equipment independently from other items of equipment. Quick and easy release may be necessary, for example, whilst the patient is transitioned from a hospital to an ambulance and vice versa.

Existing systems also do not take into account the vibrations and forces that the medical equipment may experience depending on the transportation vehicle, and the road/air conditions. These issues are confounded by the requirement that certain medical equipment have components that must be prominently displayed during transportation and/or accessible by transportation personnel. Further, certain equipment is not designed for transportation and therefore do not have handles for ease of transportation.

Therefore, there is a need for support systems suitable for supporting equipment, such as medical equipment in a stacked configuration, and which overcome or reduce at least some of the above-described problems.

SUMMARY

Embodiments of the present technology have been developed based on inventors' appreciation of at least one shortcoming associated with the prior art approaches to support systems for equipment.

Accordingly, from a first aspect of the present disclosure, there is provided a support system for supporting equipment, the support system comprising: a back support; a plurality of shelves spaced from one another and extending from the back support, a given shelf of the plurality shelves arranged to support a given unit of equipment and comprising: a connecting mechanism for providing a connected position in which the given unit of equipment is connected to the given shelf such that separation of the given shelf and the given unit of equipment along a first axis is blocked but relative movement along a second axis is possible; a locking mechanism for providing a locked position in which relative movement of the given unit of equipment and the given shelf along the second axis is blocked; and a release mechanism for releasing the locked position to permit the relative movement along the second axis, the release mechanism including an actuator on the given shelf or the given unit of equipment which can be actuated by a user.

In certain embodiments, the back support and the given shelf are positioned at substantially 90 degrees to one another, and wherein, in use, the back support is arranged to be positioned substantially vertically and the plurality of shelves are arranged to be positioned substantially horizontally, one above each other.

In certain embodiments, the first direction is a vertical direction and the second direction is a horizontal direction.

In certain embodiments, the equipment comprises an adaptor which can be connected to medical equipment, and optionally further comprising the adaptor.

In certain embodiments, the support system further comprises the equipment, and optionally wherein the equipment is an infusion pump.

In certain embodiments, the connecting mechanism comprises inter-engaging portions to mechanically connect the given unit of equipment and the given shelf in the connected position.

In certain embodiments, the inter-engaging portions comprise a tongue and groove.

In certain embodiments, the tongue and the groove are positioned along side edges of the given shelf and the given unit of equipment.

In certain embodiments, the tongue comprises a lip at a side edge of the shelf, and the groove comprises a groove formed on an inner side of a side edge of the equipment.

In certain embodiments, the locking mechanism comprises a retractable tongue for engagement in a notch, the retractable tongue actuatable between an extended position and a retracted position using the actuator.

In certain embodiments, the retractable tongue is resiliently biased to the extended position.

In certain embodiments, the retractable notch is provided on the given shelf and the notch is defined in the side wall of the given unit of equipment.

In certain embodiments, the release mechanism comprises: an actuator component including the actuator; a tongue component including the retractable tongue; wherein the actuator component and the tongue component are connected by a pin and groove assembly such that actuating the actuator causes retraction of the tongue.

In certain embodiments, the support system further comprises a top plate extending from an upper end of the back support and a bottom plate extending from a lower end of the back support. In certain embodiments, the top plate has an opening formed therein to define a handle.

In certain embodiments, the support system further comprises a handle extending from the top plate.

In certain embodiments, the support system further comprises an IV pole holder.

In certain embodiments, the support system further comprises at least one foot extending from the bottom plate.

In certain embodiments, the support system further comprises a mounting mechanism for mounting the support system to a support surface.

In certain embodiments, the mounting mechanism comprises a coupling device having a base member and a release member, the support system further comprising the release member connected to the support system.

In certain embodiments, the release member is connected to one or more of: an outer side of the back support, and lower end of the support system, and an upper end of the support system.

In certain embodiments, the support system further comprises the base member of the coupling device, the base member and the release member being releasably connectable together in a coupled position, the base member being connectable to the support surface and having: a front face including a planar contact portion for contacting the contact face of the release member; a shoulder extending around a portion of a periphery of the planar portion to define a pocket for receiving the release member, the shoulder engageable with a portion of the flange of the release member when the release member is positioned on the base member; an open access end through which the release member can be slidingly inserted and removed from the pocket; a stop member positioned in a recess within the planar contact portion and moveable by a resilient lock mechanism and an actuator between a lock position in which at least a portion of the stop member extends from the recess and abuts an edge of an opening defined in the release member contact face in the coupled position, and a release position in which the stop member is retracted into the recess; the actuator having a neutral position and a deployed position, wherein when the actuator is in the neutral position, the stop member is resiliently biased towards the lock position.

In certain embodiments, the base member comprises a plurality of spring loaded ball bearings partially extending from recesses formed in the front face of the base member and engageable with corresponding recesses defined in the planar contact face of the release member.

In certain embodiments, the release member comprises a plate-like body with a first side, the first side defining a planar contact face, and a second side having a collar extending therefrom, the collar positioned inwardly of a perimeter of the release member to define a flange portion.

In certain embodiments, the planar contact face of the release member has an anti-friction layer.

In certain embodiments, the support system further comprises a damping member attachable to a back face of the base member and arranged to be positioned between the base portion and the surface in use, the damping member being arranged to absorb vibration and/or shock.

In certain embodiments, the support system further comprises a top plate attachable to the collar of the release member and attachable to the support system.

In certain embodiments, the perimeter of the plate-like body of the release member is circular in shape, the stop member of the base member is positioned substantially centrally of the planar contact portion, and the opening of the release member is positioned substantially centrally of the plate-like body, such that the release member can be rotated within the pocket when the stop member is in the lock position.

In certain embodiments, the perimeter of the plate-like body of the release member has an eccentric shape such that the release member is not rotatable in the pocket of the base member.

From another aspect, there is provided a support system for supporting equipment, the support system comprising: a back support; a plurality of shelves spaced from one another and extending from the back support, a given shelf of the plurality shelves arranged to support a given unit of equipment and comprising: a connecting mechanism for providing a connected position in which an adaptor of the given unit of equipment is connected to the given shelf such that separation of the given shelf and the given unit of equipment along a first axis is blocked but relative movement along a second axis is possible; a locking mechanism for providing a locked position in which relative movement of the given unit of equipment and the given shelf along the second axis is blocked; and a release mechanism for releasing the locked position to permit the relative movement along the second axis, the release mechanism including an actuator on the given shelf or the given unit of equipment which can be actuated by a user.

In certain embodiments, the support system further comprises the adaptor.

In certain embodiments, the support system further comprises the given unit of equipment attachable to the adaptor.

Advantages include the ability to stack equipment, such as medical equipment, in a manner allowing for them to be individually attachable and releasable. The attachment mechanism is a secure attachment that can resist vibrations and impacts. Single handed attachment and release of the equipment is possible in certain embodiments. The support equipment can permit the stacking arrangement of infusion pumps. In certain embodiments, the support equipment can permit the releasable attachment of other medical equipment such as an IV pole.

These and other aspects and features of non-limiting embodiments will now become apparent to those skilled in the art upon review of the following description of specific non-limiting embodiments in conjunction with the accompanying drawings.

DETAILED DESCRIPTION OF THE DRAWINGS

The non-limiting embodiments will be more fully appreciated by reference to the accompanying drawings, in which.

Figure 1A:
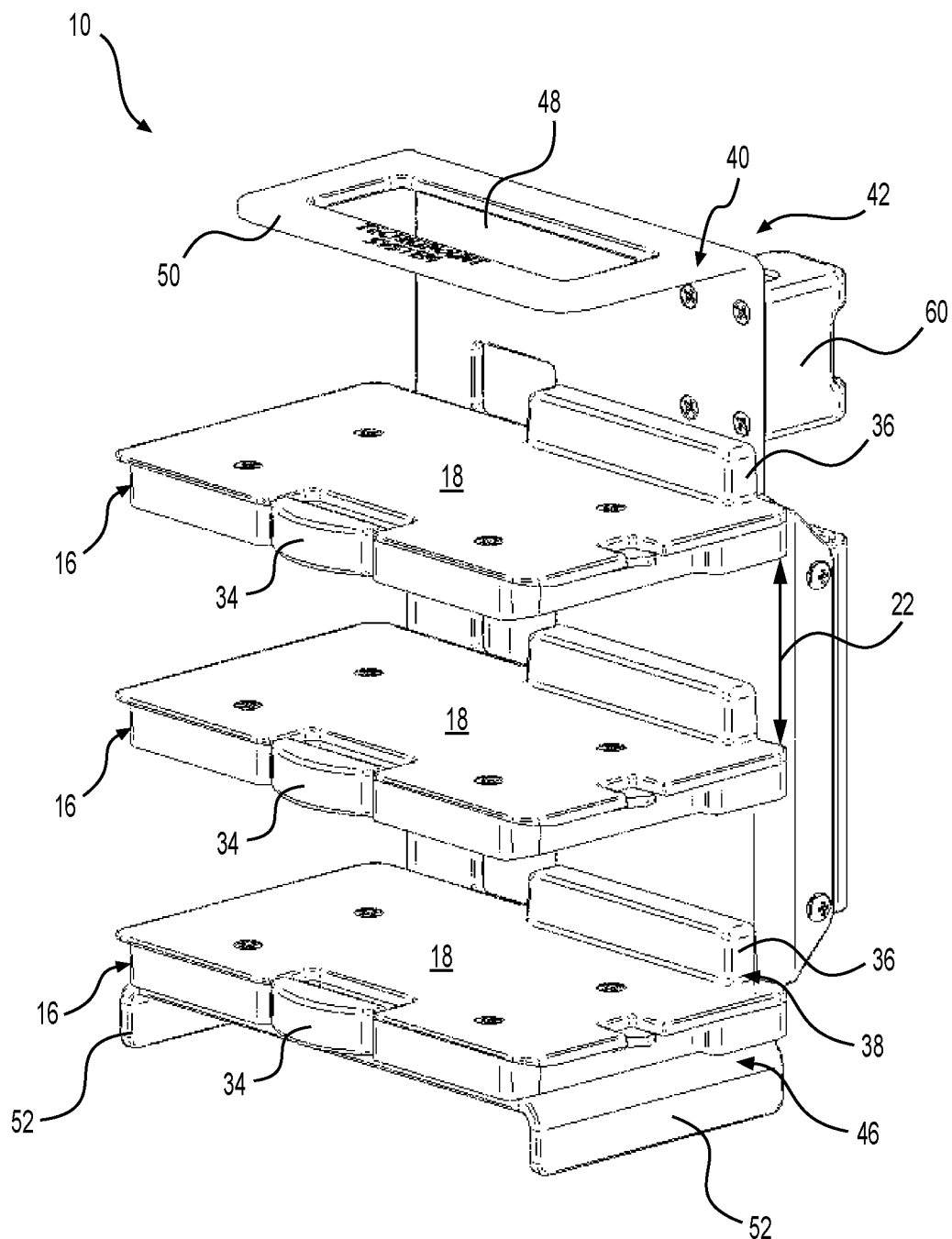
FIG. 1A is a perspective view from a front end of a support system including three shelves, according to certain embodiments of the present technology.
Figure 1B:
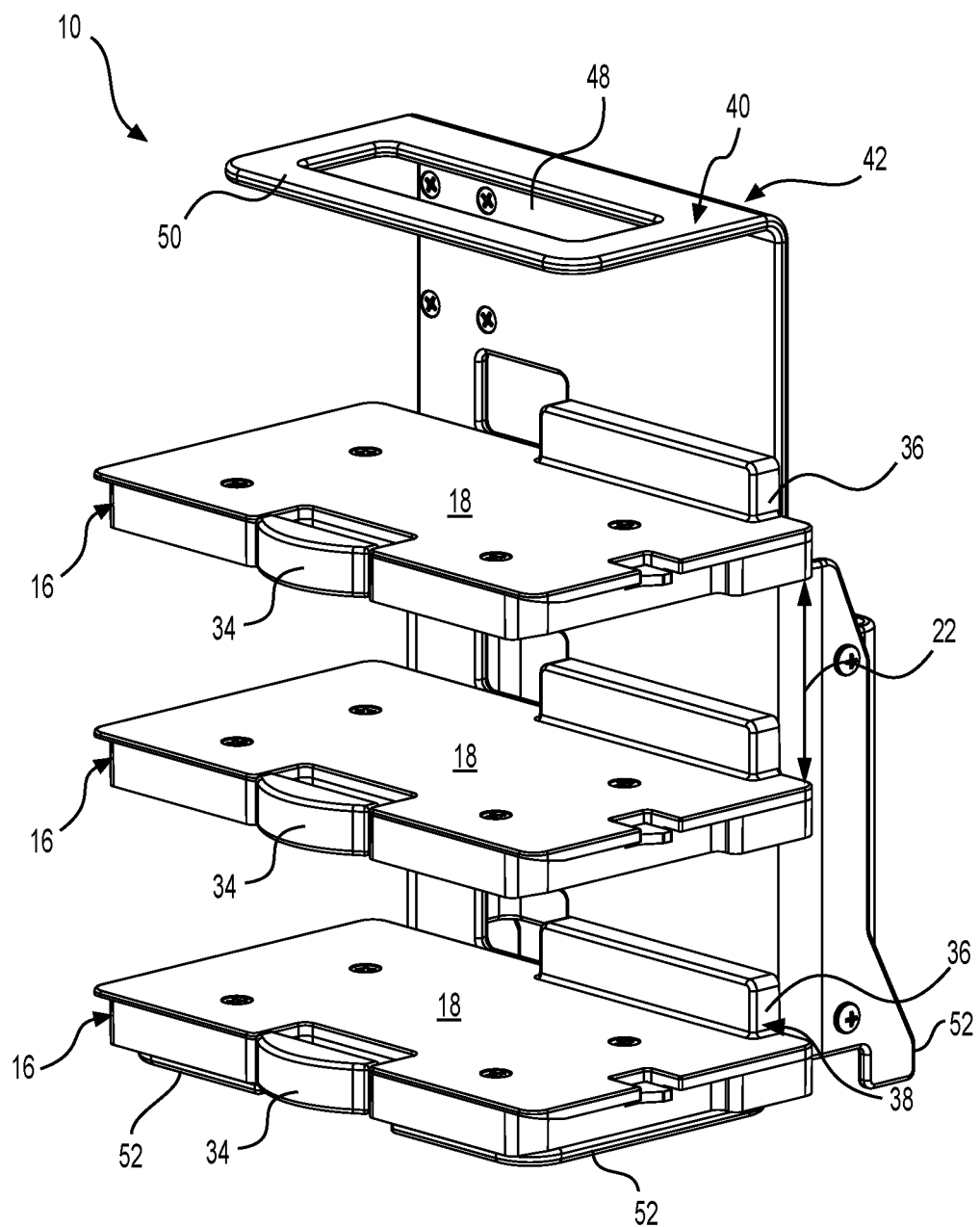
FIG. 1B is a perspective view from a front end of a support system including three shelves, according to other embodiments of the present technology.
Figure 2A:
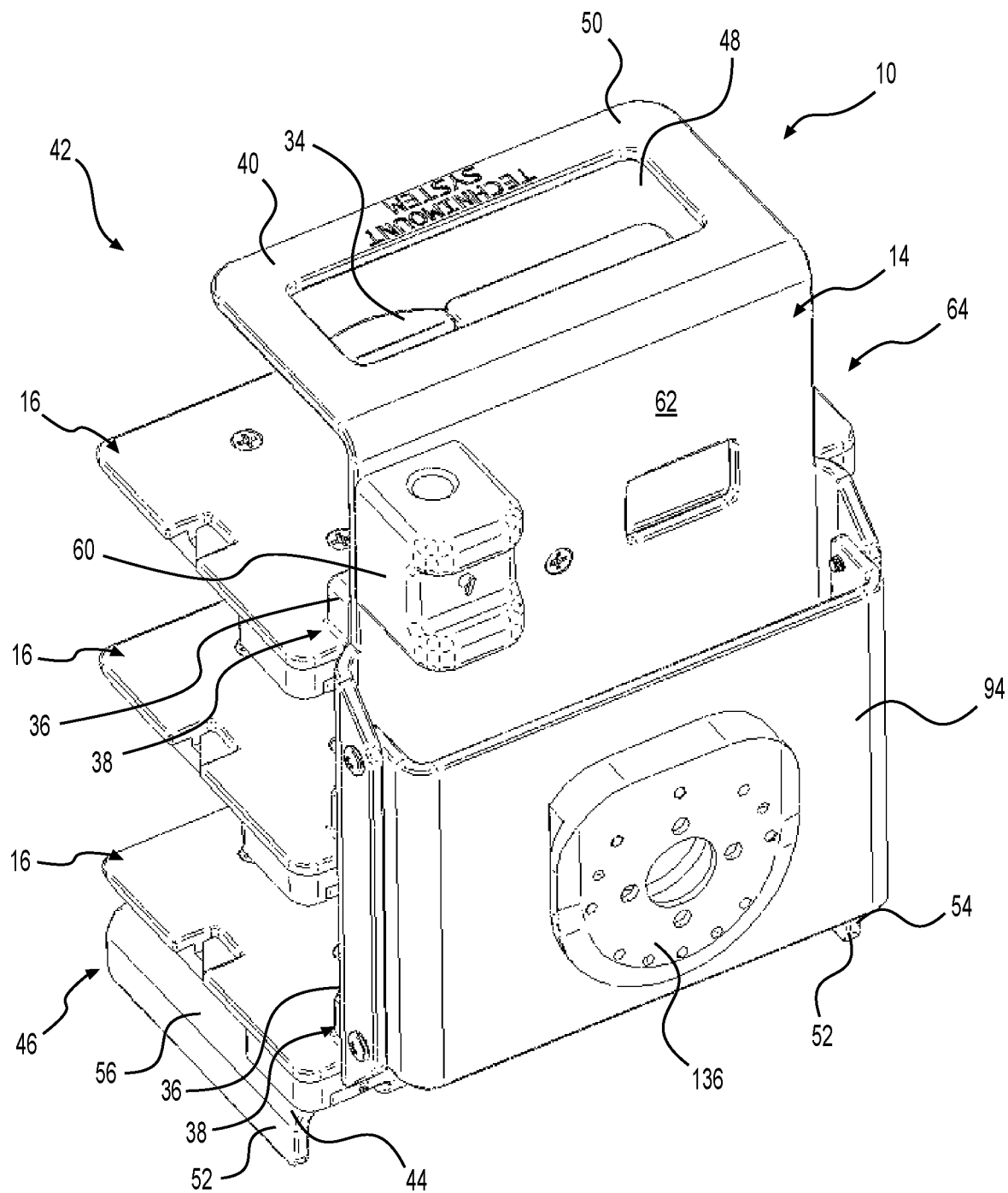
FIG. 2A is a perspective view from a back end of the support system of FIG. 1A, according to certain embodiments of the present technology.
Figure 2B:
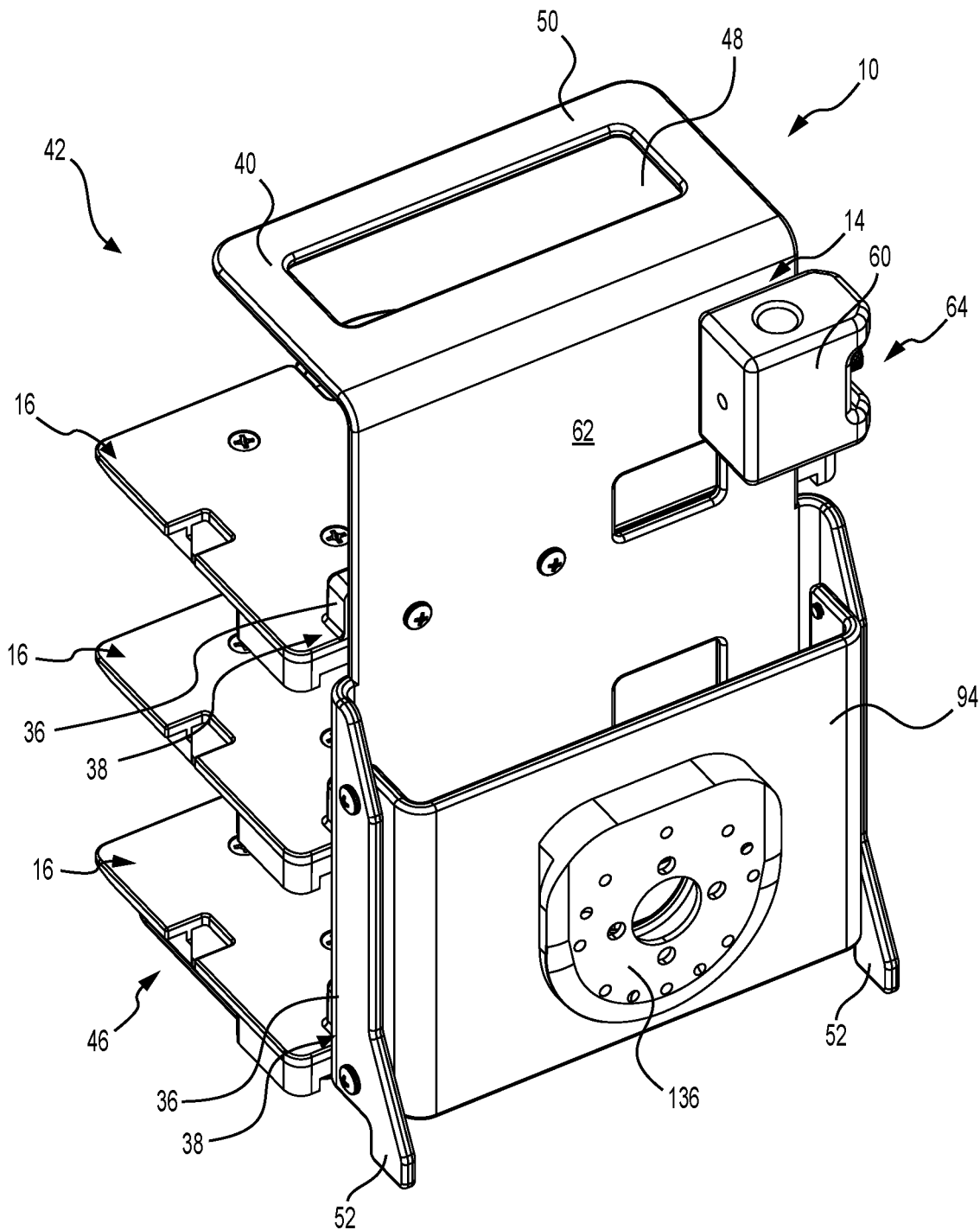
FIG. 2B is a perspective view from a back end of the support system of FIG. 1B, according to other embodiments of the present technology.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION OF THE NON-LIMITING EMBODIMENT(S)

Reference will now be made in detail to various non-limiting embodiment(s) of a support system for supporting equipment. It should be understood that other non-limiting embodiment(s), modifications and equivalents will be evident to one of ordinary skill in the art in view of the non-limiting embodiment(s) disclosed herein and that these variants should be within scope of the appended claims. Furthermore, it will be recognized by one of ordinary skill in the art that certain structural and operational details of the non-limiting embodiment(s) discussed hereafter may be modified or omitted (i.e. non-essential) altogether. In other instances, well known methods, procedures, and components have not been described in detail.

Referring initially to FIGS. 1A-4B, according to non-limiting embodiments of the present technology, there is provided a support system 10 for supporting a plurality of units of equipment 12, which may or may not be mobile. Broadly, the support system 10 is arranged to support the units of equipment 12 in a stacked configuration and in a manner allowing for independent attachment and release of each one of the units of equipment 12. The support system 10 is arranged to support each one of the units of equipment 12 in a secure manner during transportation of the equipment as well as at rest.

As illustrated and described herein, in certain embodiments, the support system 10 is for use with medical equipment, such as infusion pump devices. However, the units of equipment 12 can be any type of equipment that is required to accompany a patient, such as ventilators, pumps, monitoring equipment, screen, drips, etc. The units of equipment 12 may also be non-medically related or a combination of medical and non-medical. The support system 10, in certain embodiments, is arranged to be releasably fastened to a support surface in a patient transportation system 13 such as one or more of a stretcher (FIG. 11), a wheel chair, a portable bed, an ambulance, a fire engine, a train, a plane, a helicopter, and a ship. The support system 10 allows the attachment and release of the units of equipment 12 thereto without requiring tools. The support system 10 can be operated by a single user.

The support system 10 comprises: a back support 14 and at least one shelf 16 for supporting the unit of equipment 12. As illustrated in FIGS. 1A-4B, there are provided three shelves 16. Each shelf 16 has a top face 18 and a bottom face 20 and is arranged to support the unit of equipment 12 on its top face 18. Each shelf 16 of the support system 10 is arranged to support a different unit of equipment 12. In certain other embodiments, there are provided less than three shelves 16 or more than three shelves 16. The shelves 16 may be the same or a different configuration than one another. Each shelf 16 extends substantially transversely from the back support 14. When there is more than one shelf 16, a spacing 22 between the shelves 16 is arranged according to a size and shape of the unit of equipment that the given shelf 16 is intended to support. The spacing 22 between different shelves 16 may be different to accommodate different sizes of the units of equipment 12. The spacing 22 between different shelves 16 may be adjustable in certain embodiments. The shelves 16 may be removeable from the back support 14 and repositionable, in order to accommodate different sizes and shapes of units of equipment 12.

In certain embodiments, and as illustrated, the back support 14 is arranged to be positioned substantially vertically and the shelves 16 are arranged to be positioned substantially horizontally, one above each other. The shelves 16 are vertically aligned. In other embodiments (not shown), the shelves 16 are vertically staggered. In yet other embodiments (not shown), the support system 10 may be configured to stack the units of equipment along a horizontal axis.

Figure 3A:
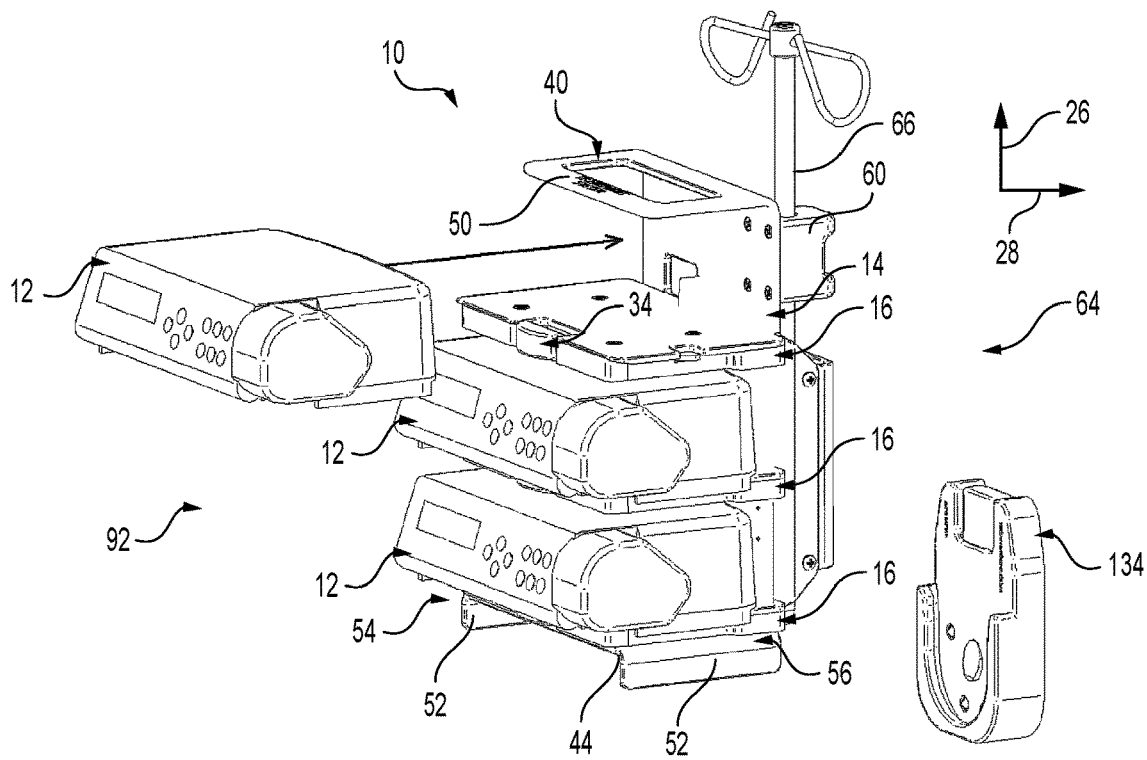
FIG. 3A is a perspective view from the front end of the support system of FIG. 1A and including three units of equipment and a base member of a coupling device, according to certain embodiments of the present technology.
Figure 3B:
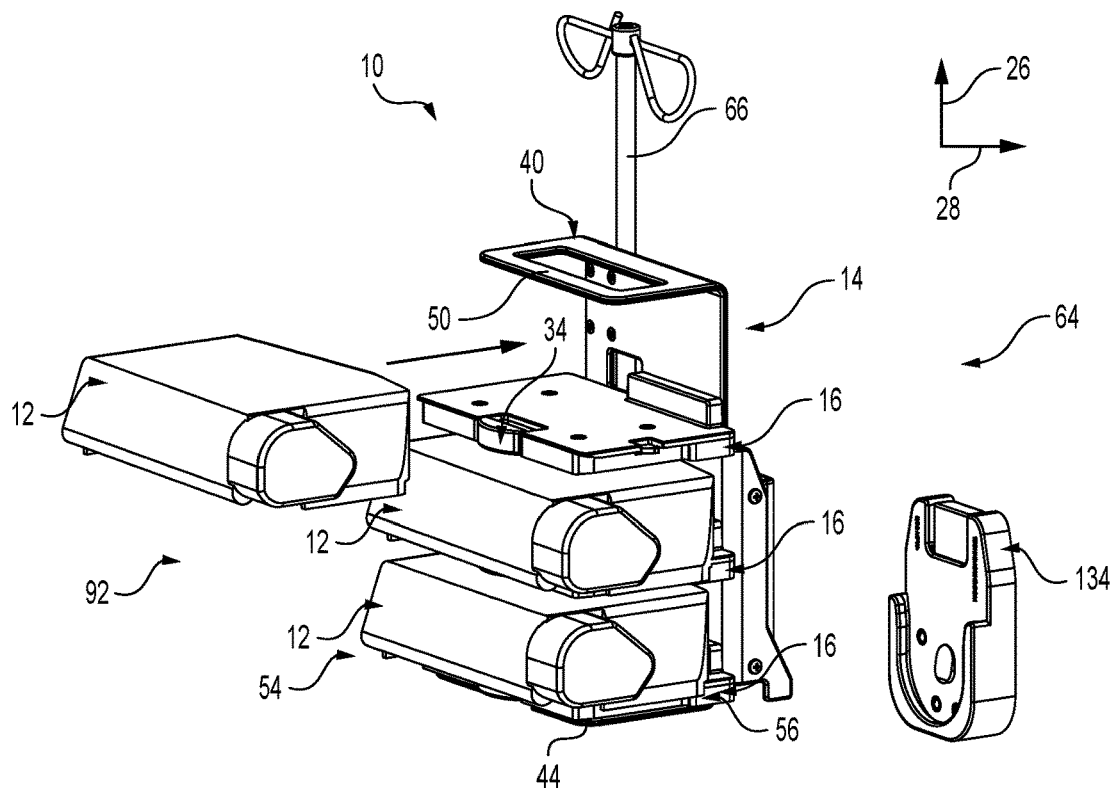
FIG. 3B is a perspective view from the front end of the support system of FIG. 1B and including three units of equipment and a base member of a coupling device, according to other embodiments of the present technology.
Figure 4A:
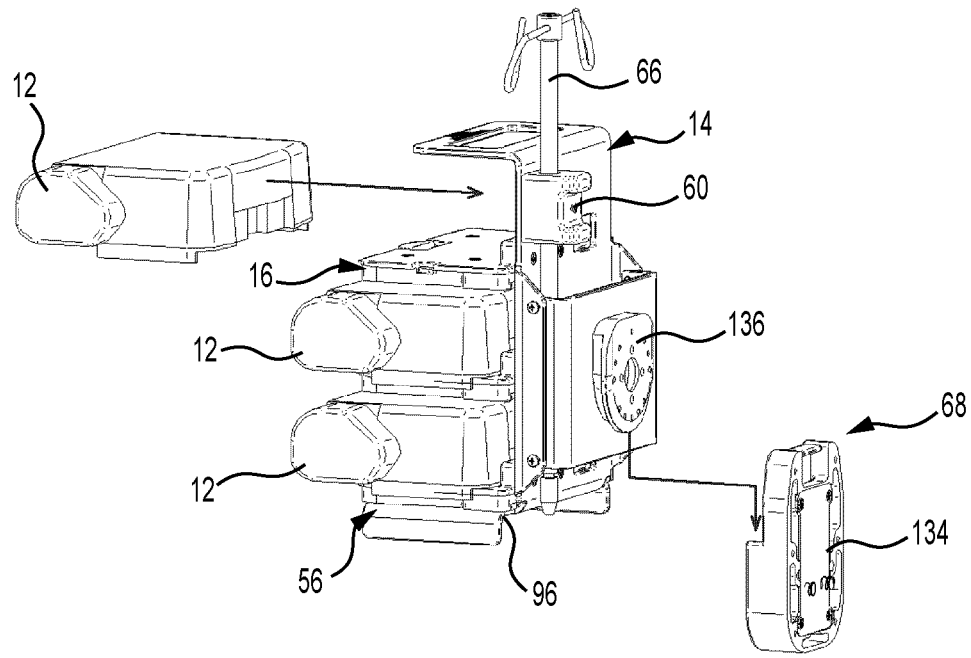
FIG. 4A is a perspective view from the side of the support system of FIG. 3A and including a release member of the coupling device, according to certain embodiments of the present technology.
Figure 4B:
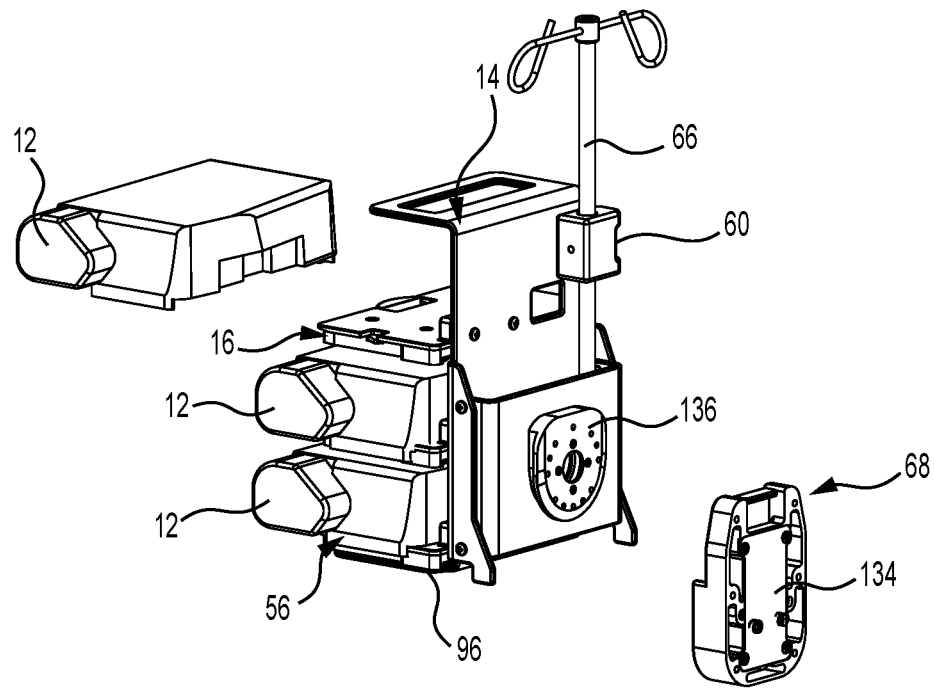
FIG. 4B is a perspective view from the side of the support system of FIG. 3B and including a release member of the coupling device, according to other embodiments of the present technology.

A connecting mechanism 24 is provided for connecting the given unit of equipment 12 to the given shelf 16 in a connected position in which separation of the given shelf 16 and the given unit of equipment 12 along a first axis 26 is blocked but relative movement along a second axis 28 is possible. Referring to FIGS. 3A and 3B, the lower two units of equipment 12 are in the connected position, respectively, on the lower two shelves 16. The first axis 26 is a vertical axis, and the second axis 28 is a horizontal axis. In other words, each unit of equipment 12 can be slid backwards and forwards relative to the shelf 16 on a horizontal plane but cannot be moved upwardly and downwardly along a vertical plane. However, in other embodiments (not shown), the first axis 26 is a horizontal axis, and the second axis 28 is a vertical axis, such as when the support system 10 is used to stack the units of equipment 12 along a horizontal plane. The connecting mechanism 24 will be described further below with reference to FIGS. 7-9.

There is also provided a locking mechanism 30, defining a locked position, in which relative movement of the given unit of equipment 12 and the given shelf 16 along the second axis 28 is prevented. A release mechanism 32, including an actuator 34, permits release of the locked position for allowing relative movement of the given unit of equipment 12 and the shelf 16 along the second axis 28. The locking mechanism 30 and the release mechanism 32 will be described further below with reference to FIGS. 7-9.

A stopper 36 is provided at a back end 38 of each shelf 16 for delimiting relative movement, in one direction, along the second axis 28. The unit of equipment 12 will abut the stopper 36 when in the locked position.

Figure 5:
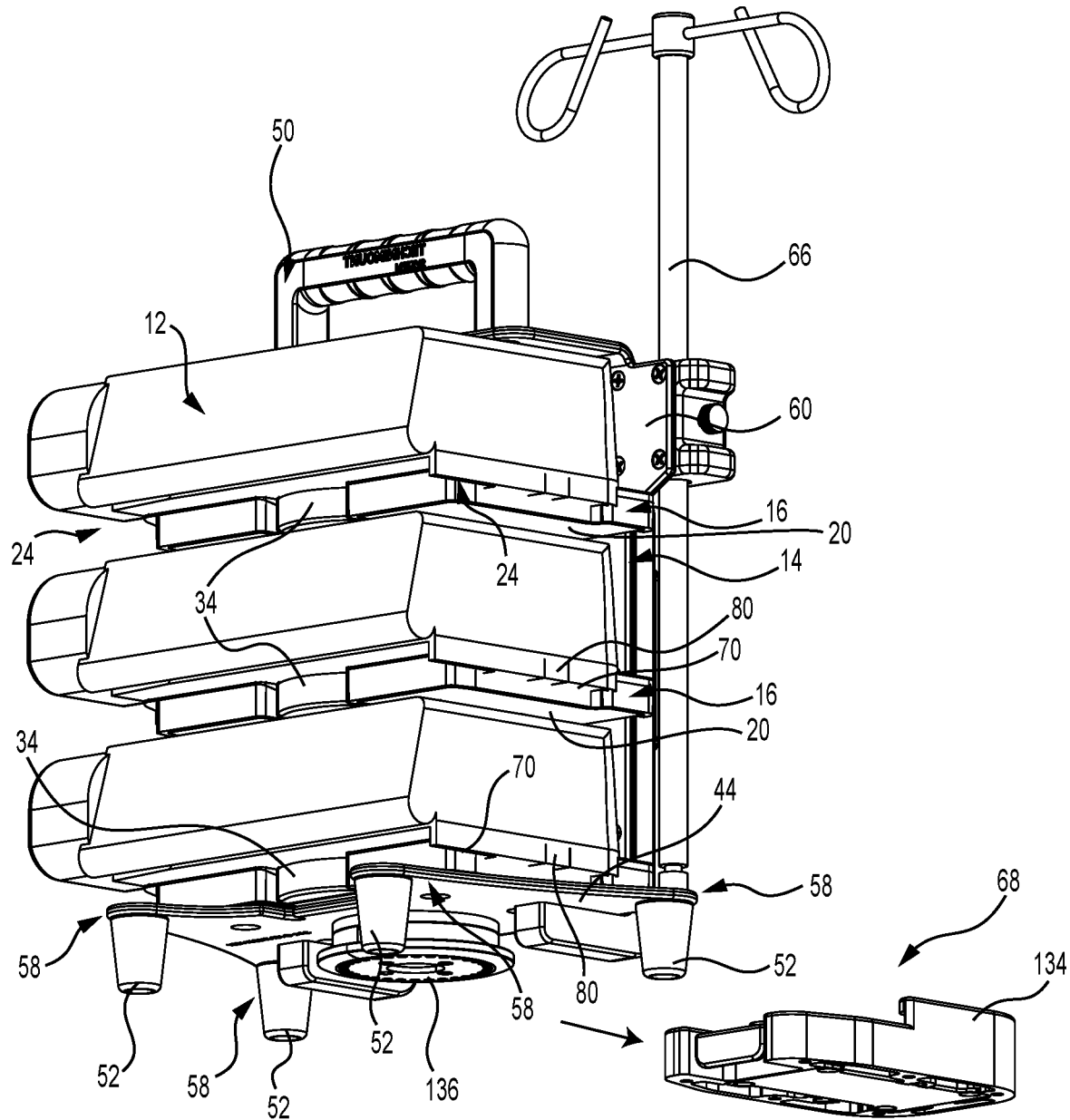
FIG. 5 is a perspective view from a front end of a support system and including a release member of a coupling device connected to the support system, and a base member of the coupling device, according to certain other embodiments of the present technology.
Figure 6A:
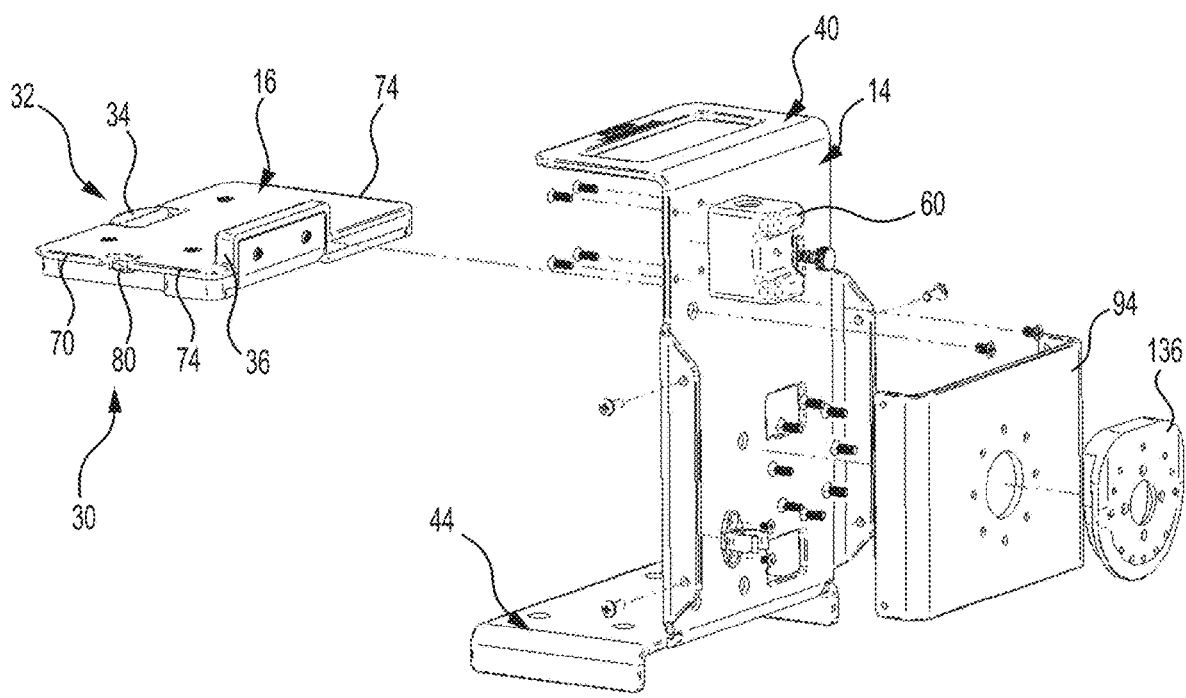
FIG. 6A is an exploded view of the support system of FIG. 1A and including a release member of a coupling device, according to certain embodiments of the present technology.
Figure 6B:
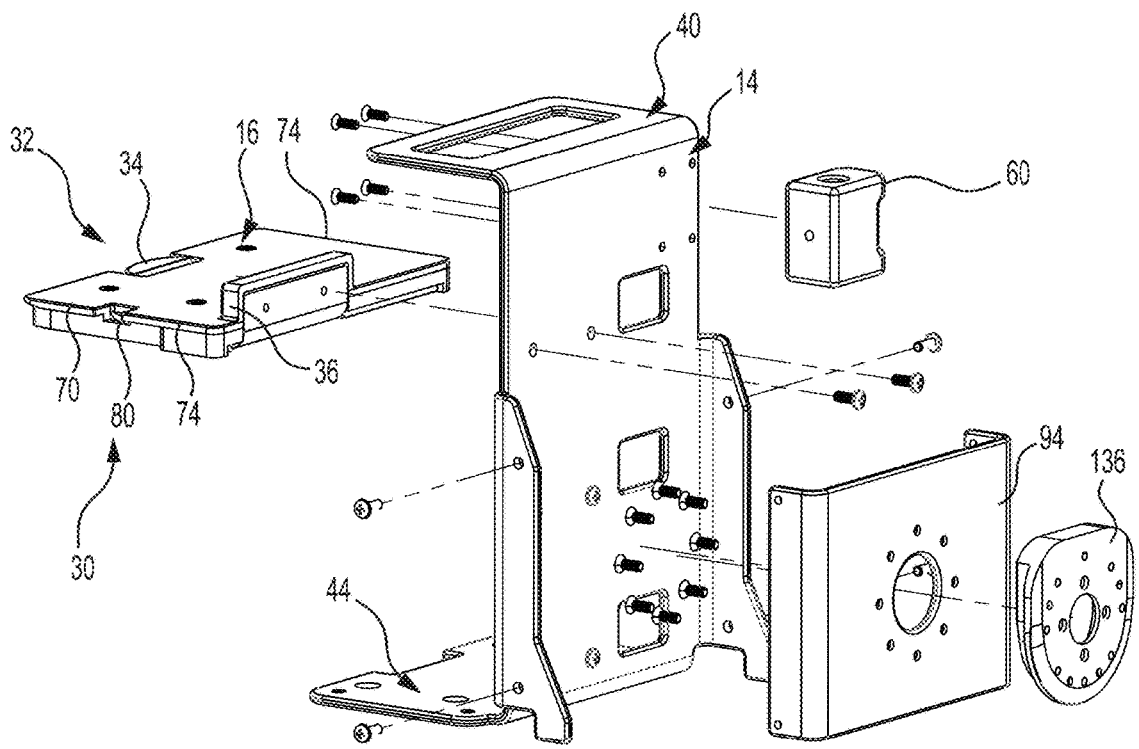
FIG. 6B is an exploded view of the support system of FIG. 1B and including a release member of a coupling device, according to other embodiments of the present technology.
Figure 11:
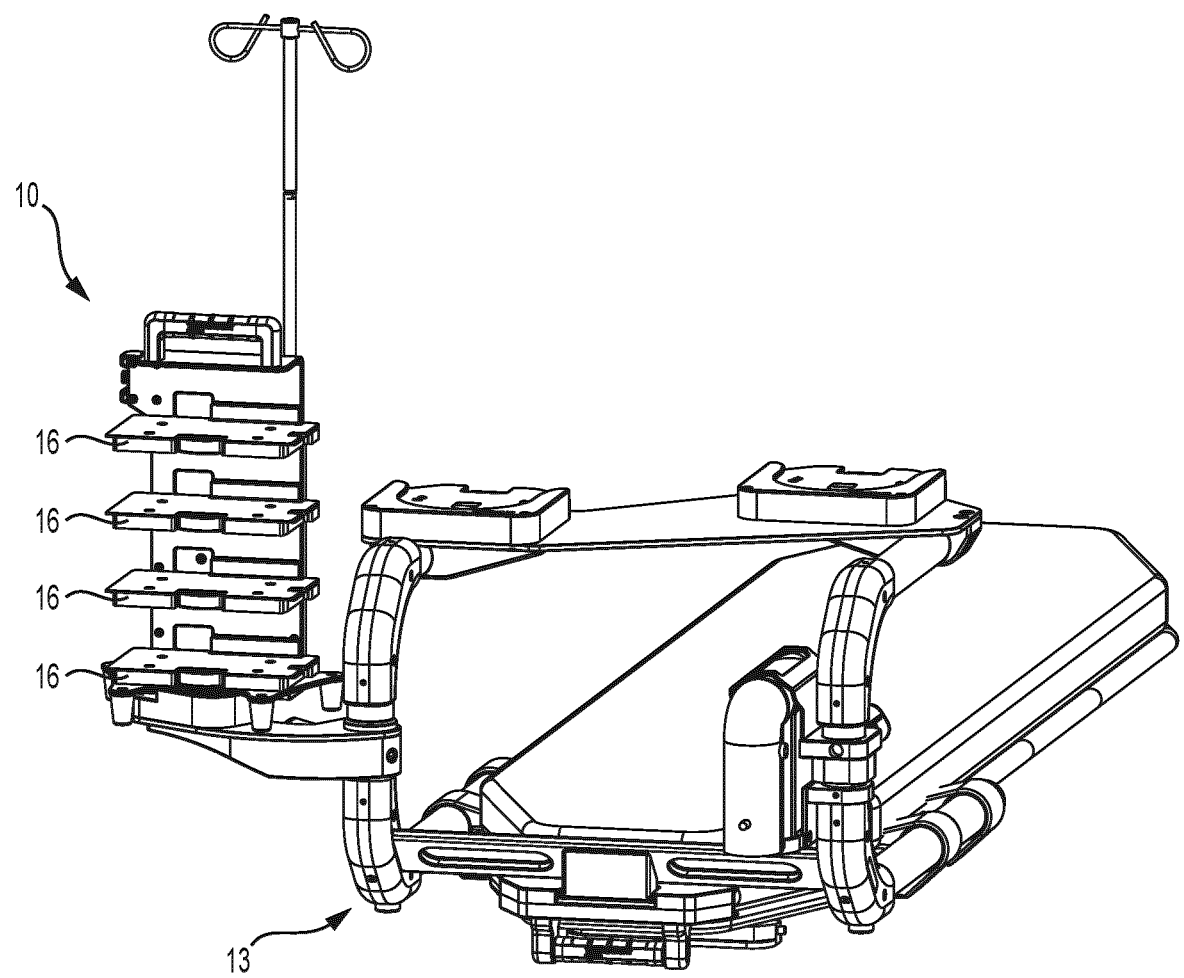
FIG. 11 is a perspective view from a front end of the support system of FIG. 5 attached to a stretcher, according to certain embodiments of the present disclosure.

The support system 10 comprises a top plate 40 extending from an upper end 42 of the back support 14 and a bottom plate 44 extending from a lower end 46 of the back support 14. The top plate 40 and the bottom plate 44 extend substantially horizontally from the back support 14 and are parallel to one another. In the embodiment of FIGS. 1A, 2A, 3A, 4A and 6 as well as in the embodiment of FIGS. 1B, 2B, 3B and 4B, an opening 48 defining a handle 50 is formed in the top plate 40. In the embodiment of FIGS. 5 and 11, the handle 50 is provided extending upwardly from the top plate 40. Feet 52 extend from the bottom plate 44 for supporting the support system 10 on a surface and for spacing the units of equipment 12 from the surface. In the embodiment of FIGS. 1A, 2A, 3A, 4A and 6, two feet 52 are provided, one on either side 54, 56 of the bottom plate 44. In the embodiment of FIGS. 1B, 2B, 3B and 4B, two feet 52 are provided on an underside of the bottom plate 44, and two feet 52 are provided on a lower part of the back support 14. In the embodiment of FIGS. 5 and 11, four feet 52 are provided one at each corner 58 of the bottom plate 44. The top plate 40, the bottom plate 44 and the back support 14 may be one-piece.

An IV pole holder 60 is provided at an outer side 62 of the back support 14 (corresponding to a back end 64 of the support system 10) for supporting an IV pole 66 in a substantially vertical configuration.

The support system 10 is also provided with a mounting mechanism 68 for mounting the support system 10 to a support surface, such as on the patient transportation system 13. The mounting mechanism 68 comprises, in certain embodiments, a coupling device 120 having a base member 134 and a release member 136, which will be described below with reference to FIGS. 12-20. In other embodiments, other mounting mechanisms 68 may be provided such as, screw type mounting mechanisms, clamping mounting mechanisms, etc.

Figure 7:
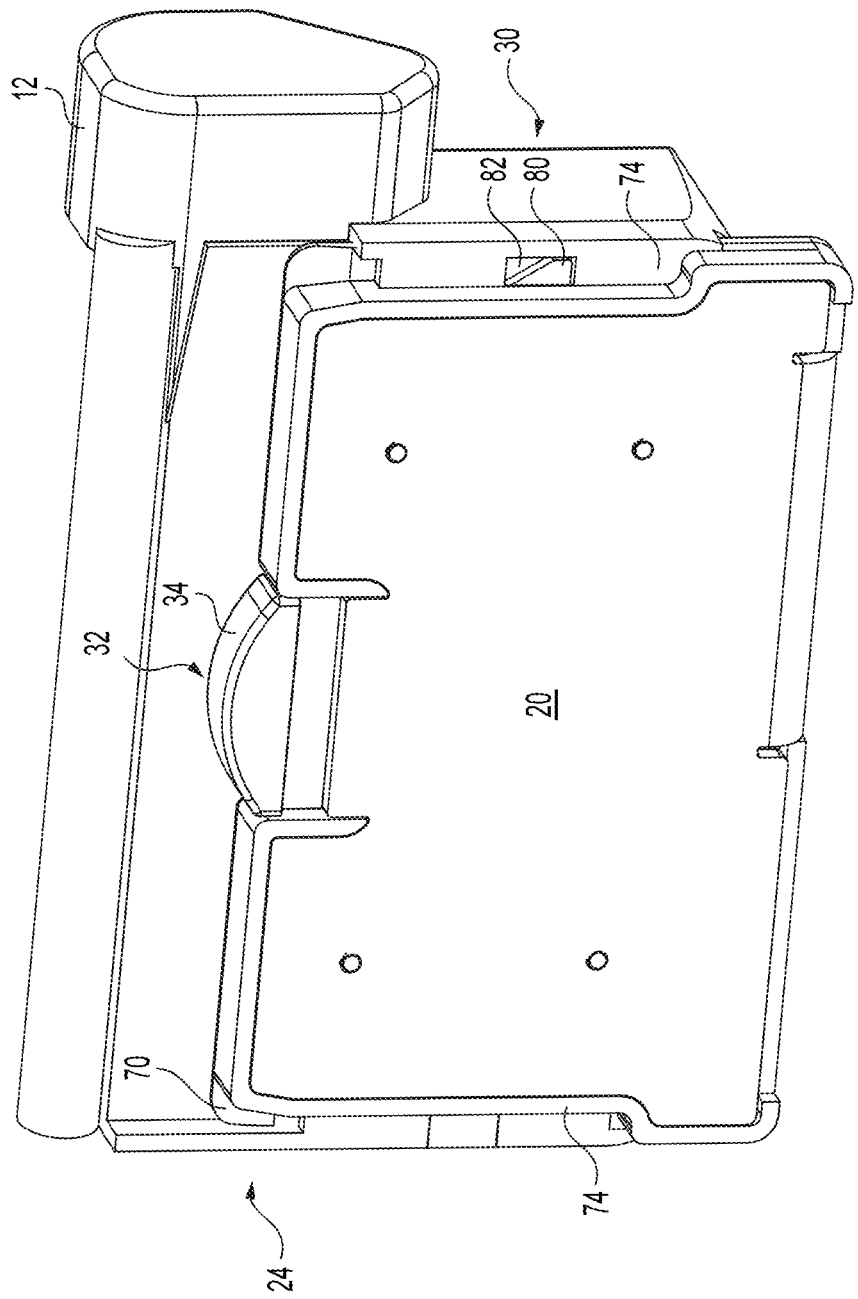
FIG. 7 is a bottom plan view of a shelf of the support system of FIG. 1 or FIG. 5 with an item of equipment attached thereto, according to certain embodiments of the present technology.
Figure 8:
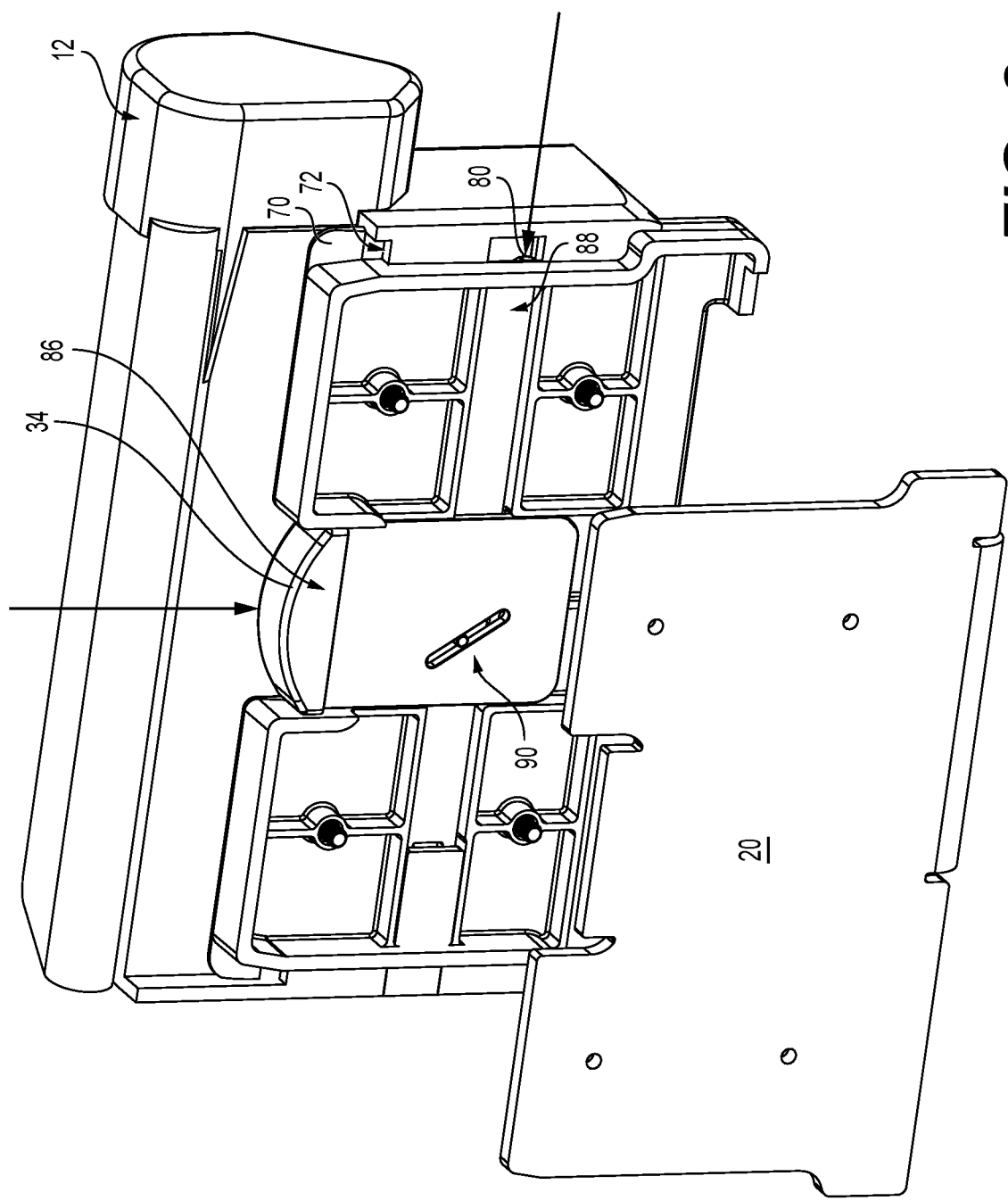
FIG. 8 is a partially exploded view the shelf of FIG. 7, according to certain embodiments of the present technology.
Figure 9:
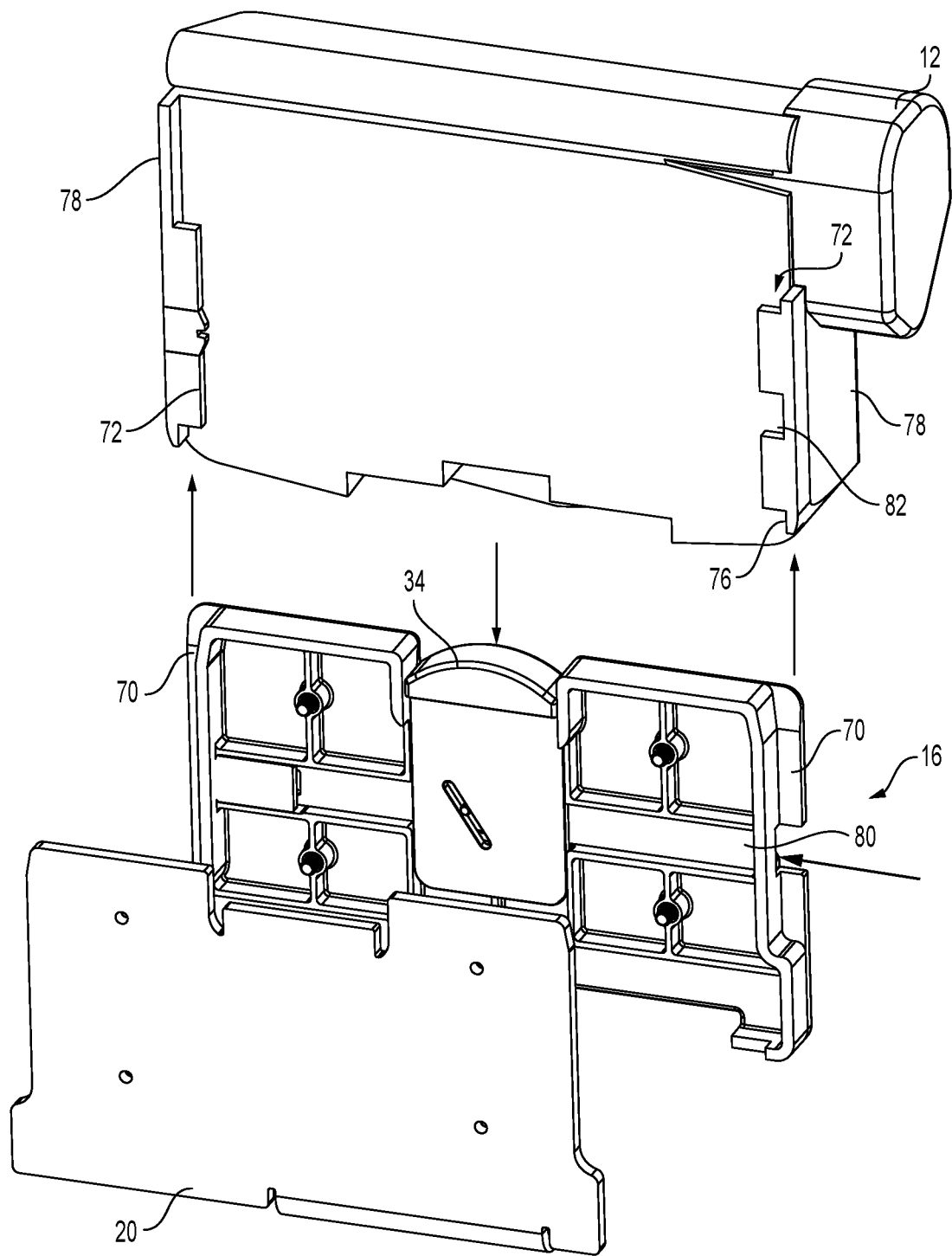
FIG. 9 is the partially exploded view of the shelf of FIG. 8 with the item of equipment separated therefrom, according to certain embodiments of the present disclosure.
Figure 10:
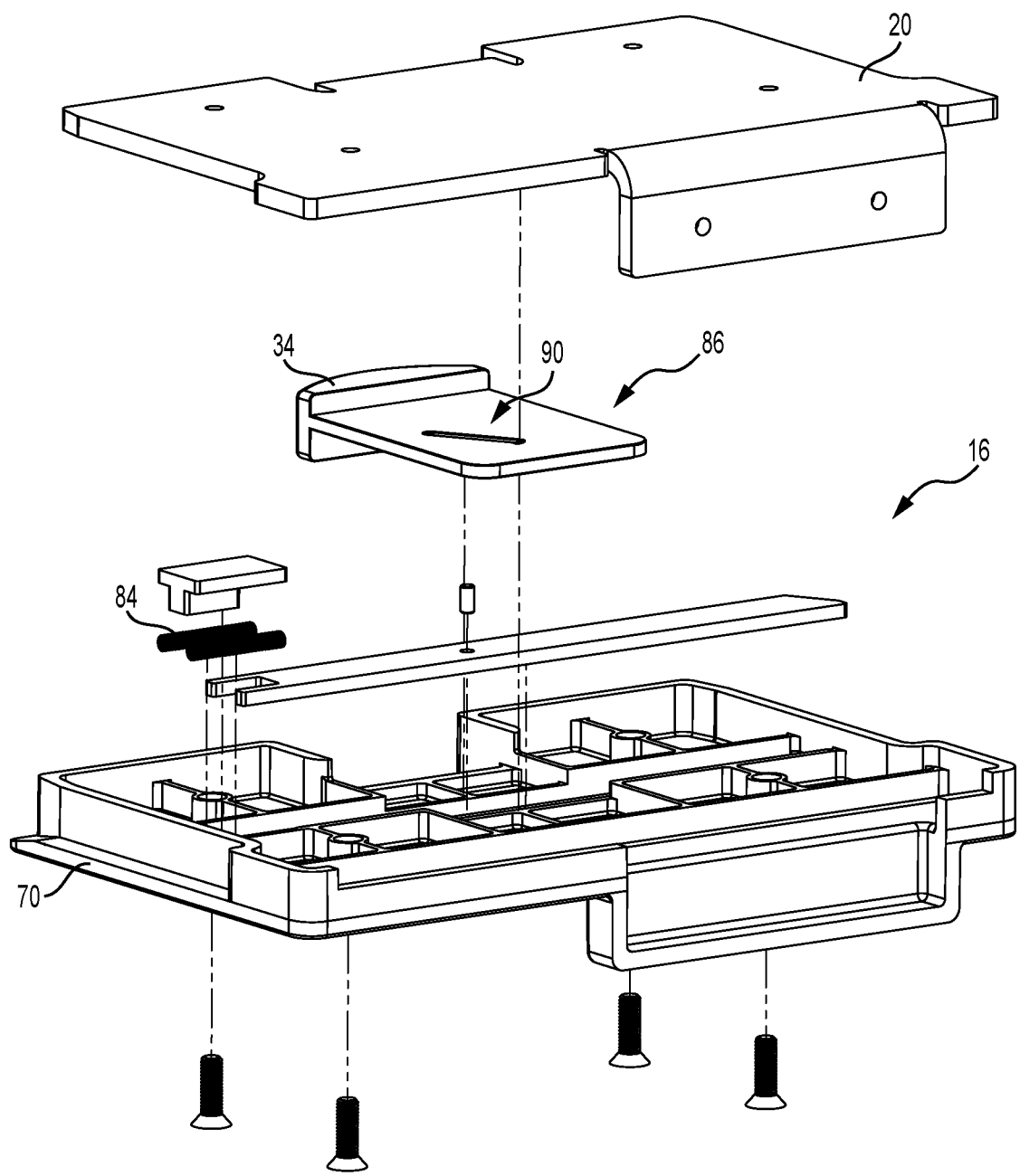
FIG. 10 is a perspective view of a bottom face of the shelf of FIG. 7, according to certain embodiments of the present disclosure.

Turning now to the connecting mechanism 24 of the support system 10, which is best seen in FIGS. 7-9. The connecting mechanism 24 comprises inter-engaging portions between the given unit of equipment 12 and the shelf 16 to mechanically connect them in the connected position. The inter-engaging portions comprise a tongue 70 and groove 72 of the given shelf 16 and the given unit of equipment 12. In the illustrated embodiments, the tongue 70 comprises a lip 70 at each side edge 74 of the shelf 16, and the groove 72 comprises a groove 72 formed on an inner side 76 of the side walls 78 of the given unit of equipment 12. This permits relative sliding movement of the given unit of equipment 12 and the shelf 16 along a horizontal plane. In other embodiments, the shelf 16 may be angled to the horizontal plane.

It will be appreciated that the connecting mechanism 24 can comprise any other arrangement permitting relative movement of the given unit of equipment 12 and the shelf 16 in a single direction. In embodiments (not shown) where the support system 10 is arranged to support equipment 12 in a horizontal stacking configuration, the connecting mechanism 24 can be suitably adapted. It will also be appreciated that in other embodiments (not shown), the tongue 70 can be provided on the given unit of equipment 12, and the groove 72 can be provided on the given shelf 16.

Turning now to the locking mechanism 30 which locks the unit of equipment 12 to the shelf 16 in the locked position such that relative movement between the unit of equipment 12 and the shelf 16 is prevented. The locking mechanism 30 comprises a retractable tongue 80 which is actuatable between an extended position and a retracted position using the actuator 34. When in the extended position, the retractable tongue 80 engages in a notch provided in the side wall 78 of the unit of equipment 12. The retractable tongue 80 is resiliently biased to the extended position such that in a rest position (when there is no actuation of the actuator 34), it extends from a perimeter of the shelf 16. A resilient member 84, such as a spring, permits the retractable tongue 80 to be pushed back into the retracted position such as when the unit of equipment 12 is being slid along the lip 70 to the connected position. Once in the connected position, the retractable tongue 80 is lined up with the notch 82, and the retractable tongue 80 extends into the notch 82 thereby locking the unit of equipment 12 into the locked position.

The release mechanism comprises 32: an actuator component 86 including the actuator 34; a retractable tongue component 88 including the retractable tongue 80; wherein the actuator component 86 and the tongue component 88 are connected by a pin and groove assembly 90 such that pushing the actuator 34 causes retraction of the retractable tongue 80. The pin and groove assembly 90 are positioned diagonally to an axis of actuation of the actuator 34.

In the illustrated embodiments, the connecting mechanism 24 and the locking mechanism 30 act between the given shelf 16 and the given unit of equipment 12. However, in other embodiments, the interaction of the given shelf 16 may be with an adaptor (not shown) of the unit of equipment 12, which adaptor can be retrofitted to existing equipment, permitting its connection thereto. In these cases, a locking mechanism is provided to lock the adaptor to the equipment.

In use, the given unit of equipment 12, can be moved towards the given shelf 16 of the support system, and slid relative to the given shelf 16 by means of the tongue 70 and groove 72 arrangement of the connecting mechanism 24. The connecting mechanism 24 also guides the movement of the unit of equipment 12 relative to the shelf 16. Movement of the unit of equipment 12 is from a front end 92 of the support system 10 towards the back end 64 along a horizontal plane. The retractable tongue 80 of the shelf 16 is caused to retract during this relative movement and until the retractable tongue 80 is lined up with the notch 82 in the unit of equipment 12 at which point it extends into the notch 82 to secure the unit of equipment 12 and the shelf in the locked position. Pushing the actuator 34 inwardly (towards the back end 64 of the support system), causes the retraction of the retractable tongue 80 and permitting the unit of equipment 12 to be slid outwardly (towards the front end 92 of the support system) and to be separated therefrom once the tongue 70 and groove 72 have been disengaged.

Turning now to FIGS. 12-20 showing the coupling device 120, which is configured to releasably attach the support system 10 to the patient transportation system 13. The coupling device 120 comprises a base member 134 connectable to a portion of the patient transportation system, and a release member 136 connectable to the equipment support system. The base member 134 and the release member 136 are releasably connectable.

The release member 136 has a body 138 which is plate-like and has a first side 140 and a second side 142. The first side 140 of the release member body 136 defines a planar contact face 144 for contacting the base member 134. The second side 142 of the release member 136 has a collar 146 extending therefrom, the collar 146 positioned inwardly of a perimeter 148 of the release member 136 to define a flange portion 150 of the release member 136.

The base member 134 has a front side 152 and a back side 154. The front side 152 has a planar contact portion 156 for contacting the contact face 144 of the release member 136. A shoulder 158 extends around a portion of a periphery 160 of the planar contact portion 156 to define a pocket 162 for receiving at least a portion of the release member 136. The shoulder 158 is engageable with a portion of the flange 150 of the release member 36 when the release member 136 is positioned on the base member 134.

The base member front side 152 has an open access end 164 through which the release member 136 can be slidingly inserted and removed from the pocket 162. As can be seen, the base member 134 is four-sided, with the shoulder 158 extending around three of the four sides and the fourth side being the open access end 164. In other embodiments, the base member 134 may have different numbers of sides.

Figure 12:
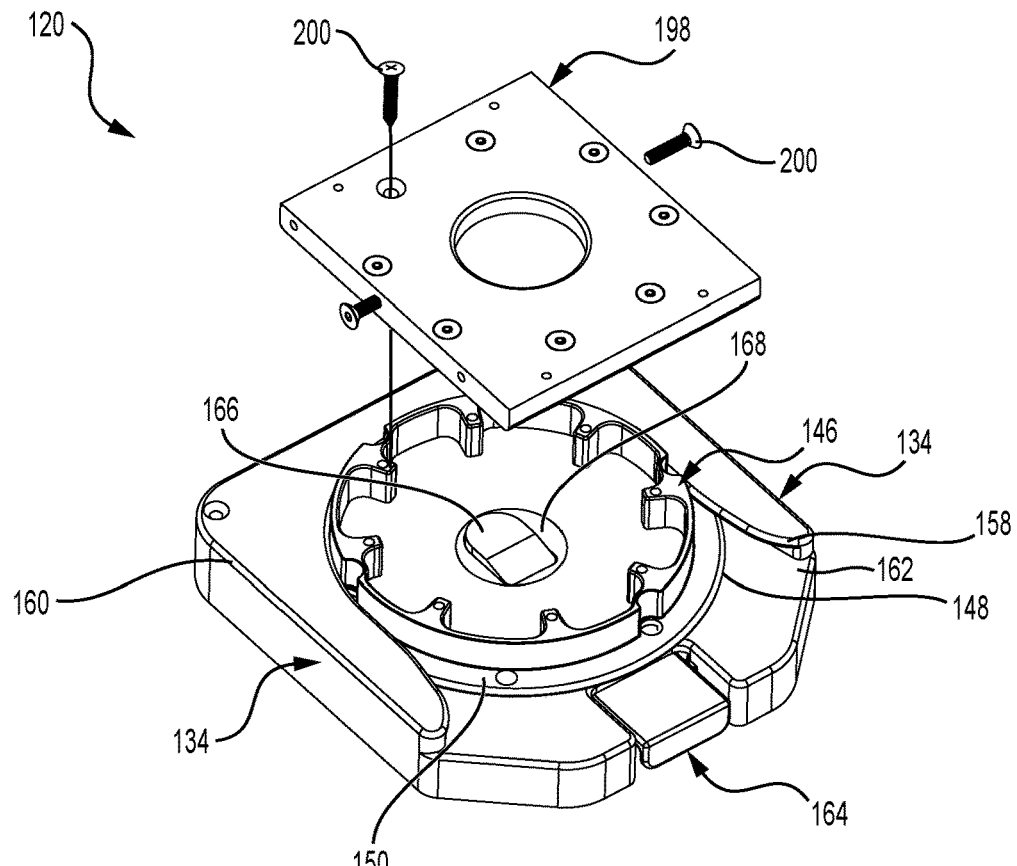
FIG. 12 is a coupling device comprising a base member, a release member, and a top plate, when the coupling device is in the coupled and lock position, according to certain embodiments of the present disclosure.
Figure 13:
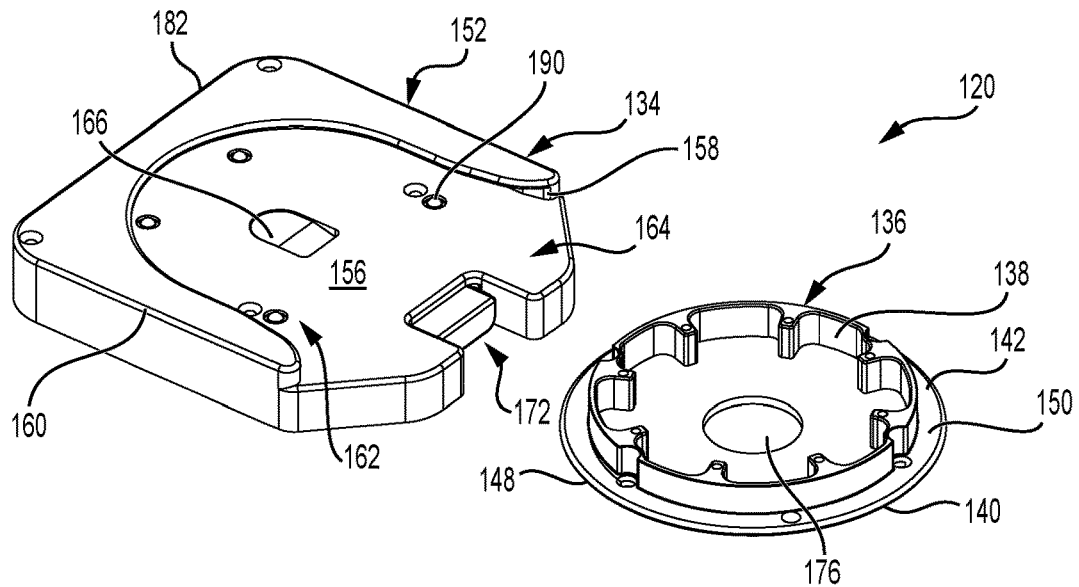
FIG. 13 is the coupling device of FIG. 12, with the top plate removed for clarity and when in the uncoupled position, according to certain embodiments of the present disclosure.

A stop member 166 is positioned in a recess 168 within the planar contact portion 156 of the base member 134 and is moveable relative to the planar contact portion 156. The stop member 166 is moveable to extend out of the recess 168 and to be housed fully in the recess 168 by a coupling lock mechanism 170 and an actuator 172. The stop member 166 is actuatable between a lock position in which at least a portion of the stop member 166 extends from the recess 168 and a release position in which the stop member 166 is retracted into the recess 168 and does not extend from the recess 168. In the lock position, when the base member 134 and the release member 136 are coupled together, the stop member 166 can abut an edge 174 of an opening 176 defined in the release member contact face 144 to delimit movement of the release member 36 towards the open access end 64 (FIG. 12). In the release position, the release member 136 can be decoupled from the base member 134 (FIG. 13).

The actuator 172 is positioned at the open access end 164. The actuator 172 is a push button 178 housed within a groove 180 formed at the open access end 164. The actuator 172 can be moved between a neutral position and a deployed position. When the actuator 172 is in the neutral position (FIG. 12), the stop member 166 is resiliently biased towards the lock position. As best seen in FIG. 13, when the actuator 172 is in the deployed position (pushed inwardly), the coupling lock mechanism 170 is arranged to move the stop member 166 to retract into the recess 168 in the release position. This can allow the release member 136 to be slid relative to the base member 134 and removed from the base member 134. In certain embodiments, the actuator 172 extends beyond a perimeter 182 of the base member 134 (FIG. 20) when in the neutral position. In other embodiments, the actuator 172 does not extend beyond the perimeter 182 of the base member 134 (FIGS. 12-13).

Figure 14:
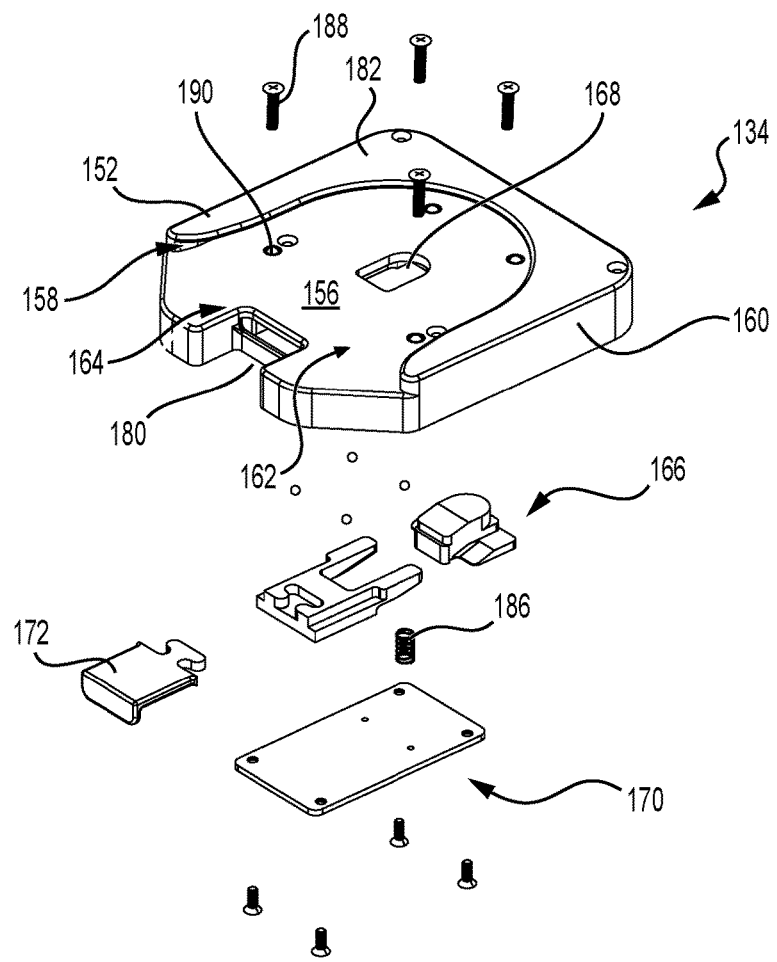
FIG. 14 is an exploded view of the base member of FIG. 12, according to certain embodiments of the present disclosure.
Figure 15:
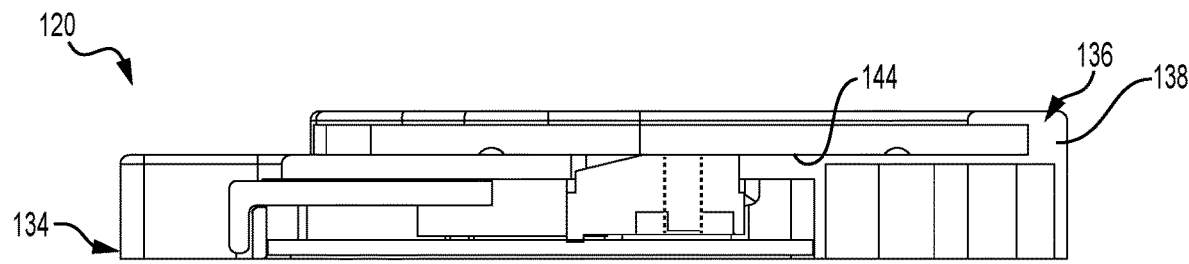
FIG. 15 is a cross-sectional view of the coupling device of FIG. 12, according to certain embodiments of the present disclosure.
Figure 16:
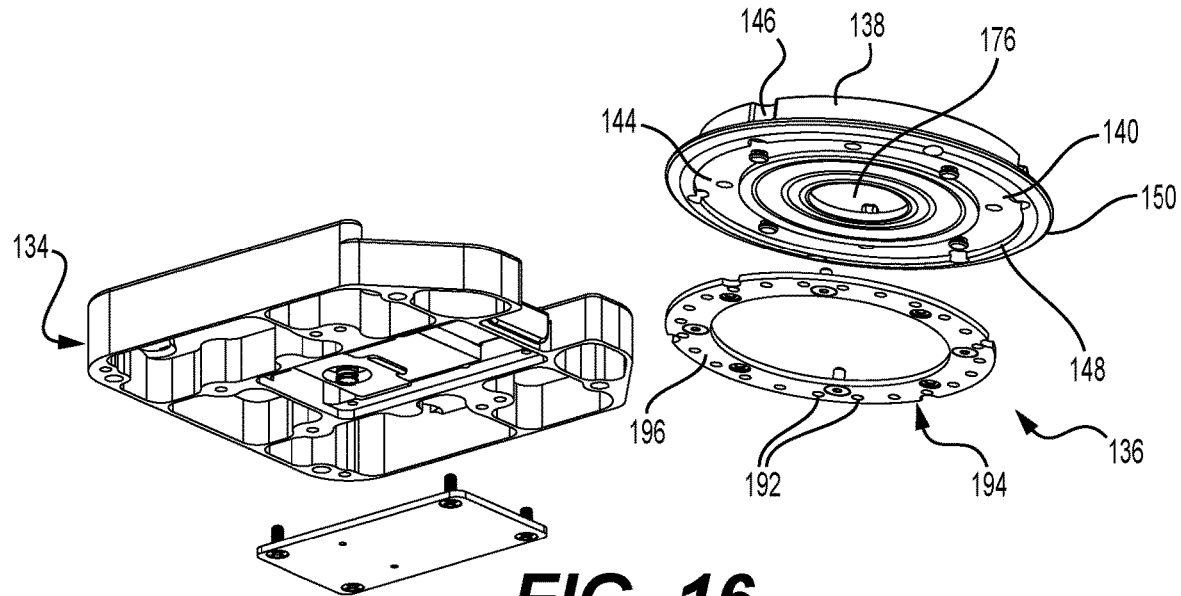
FIG. 16 is an exploded view of the base member and the release member of FIG. 12, according to certain embodiments of the present disclosure.
Figure 18:
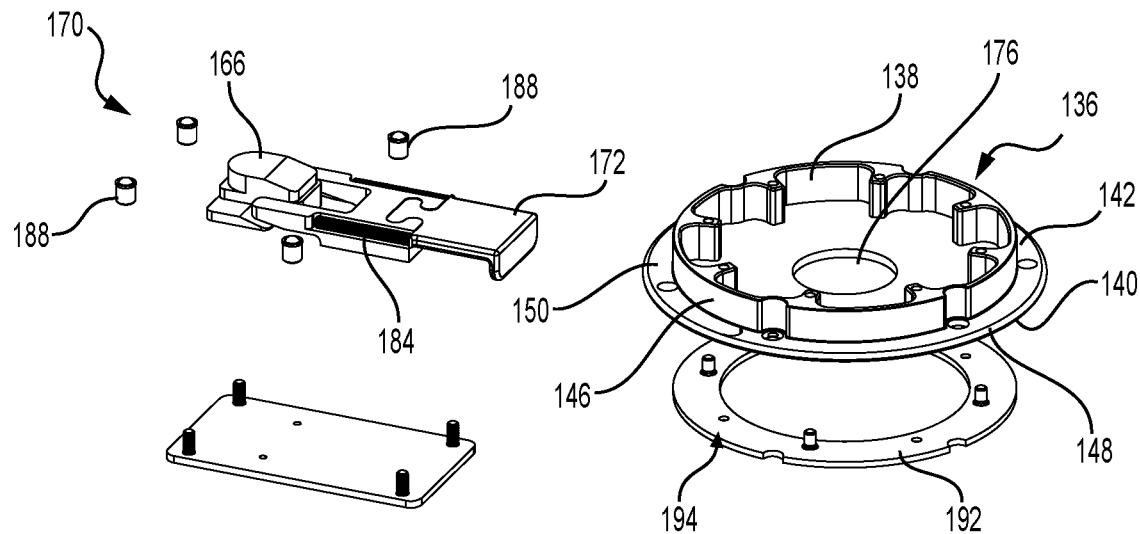
FIG. 18 is an exploded view of the release member of FIG. 12 and a lock mechanism, according to certain other embodiments of the present disclosure.
Figure 19:
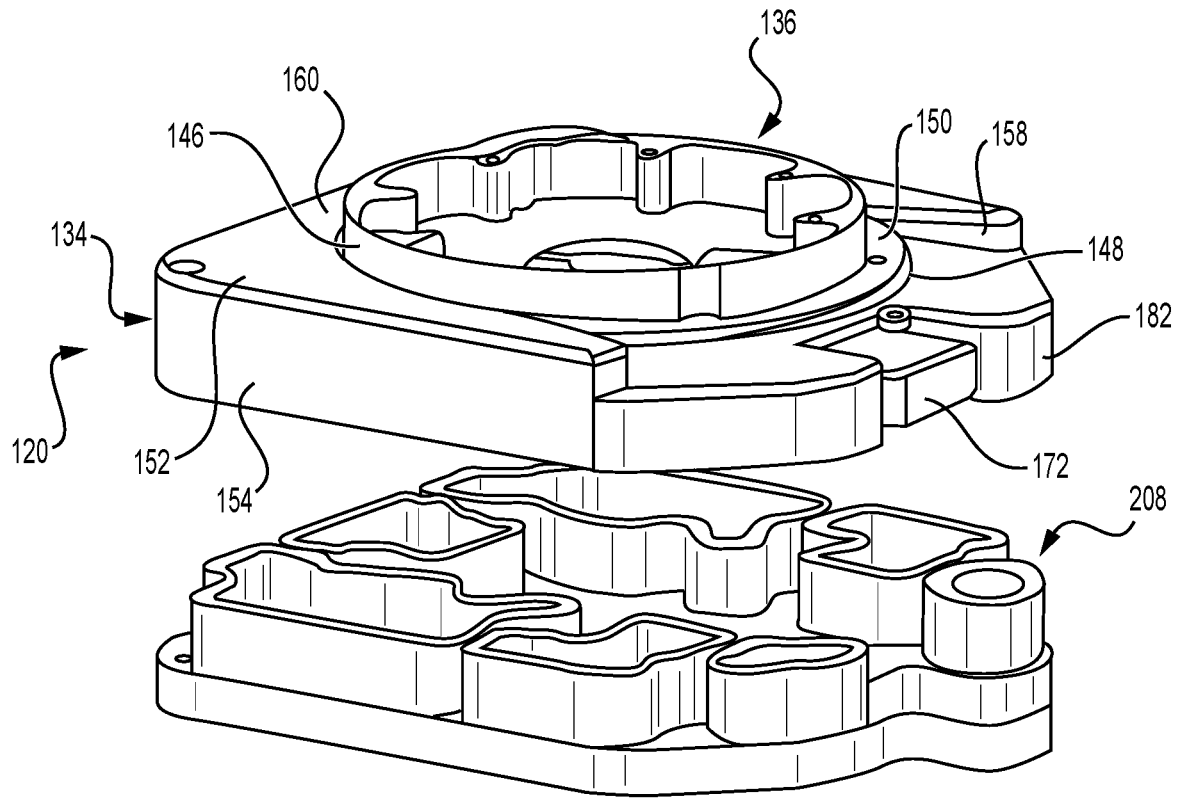
FIG. 19 is the base member of FIG. 12 and a damping member, according to certain embodiments of the present disclosure.

The coupling lock mechanism 170, best seen in FIGS. 14 and 18, comprises an actuator spring 184 resiliently biasing the actuator 172 outwardly to the neutral position, and a stop member spring 186 resiliently biasing the stop member 166 to the lock position. The actuator spring 184 and the stop member spring 186 extend in directions which are substantially transverse to one another.

The base member 134 comprises a plurality of spring loaded ball bearings 188 partially extending from recesses 190 formed in the planar contact portion 156 of the front side 152 of the base member 134 and engageable with corresponding recesses 192 defined in the planar contact face 144 of the release member 136. The spring loaded ball bearings 188 and the recesses 192 can guide the movement of the release member 136 relative to the base member 134.

Figure 17:
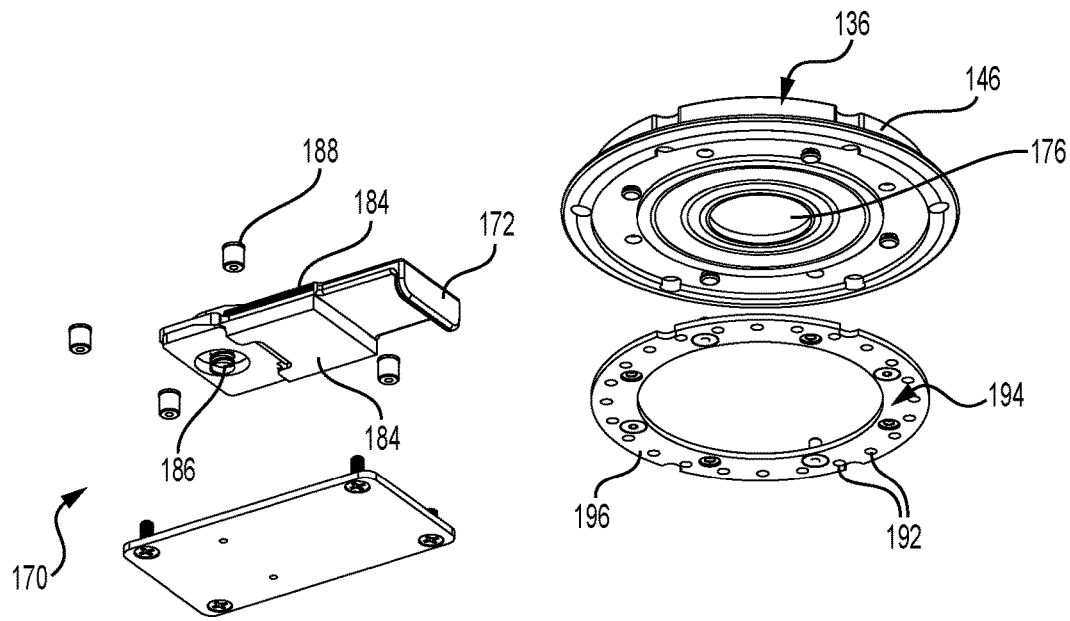
FIG. 17 is an exploded view of the release member of FIG. 12 and a lock mechanism, according to certain embodiments of the present disclosure.

In certain embodiments, the planar contact face 144 of the release member 136 comprises an anti-friction layer for reducing or minimizing friction between the contact faces 144, 156 of the release member 136 and the base member 134. As illustrated in FIGS. 17 and 18, the anti-friction layer comprises a disc 194 attached to the release member 136 and with an outer face 196 which is the planar contact face 144 and having anti-friction properties. In this embodiment, the recesses 192 for receiving the spring loaded ball bearings 188 are formed in the disc 194. In other embodiments, the anti-friction layer comprises a coating. The anti-friction layer may comprise any material that reduces friction between the base member 134 and the release member 136.

The coupling device 120 further comprises a top plate 198 attachable to the collar 146 of the release member 136 and attachable to the equipment 12. As best seen in FIG. 12, the top plate 198 is attached to the collar 146 by fasteners 200, such as screws. The top plate 198 has an opening formed therein.

In certain embodiments (for example as illustrated in FIGS. 12-19), when the base member 134 and the release member 136 are coupled together and in the lock position, the release member 136 is rotatable within the pocket 162 whilst maintaining the coupling. In this respect, the perimeter 148 of the plate-like body 138 of the release member 136 is circular in shape, the stop member 166 of the base member 134 is positioned substantially centrally of the planar contact portion 156, and the opening 176 of the release member 136 is positioned substantially centrally of the plate-like body 138, such that the release member 136 can be rotated within the pocket 162 when the stop member 166 is in the lock position. The stop member 166 can be considered to function also as a pivot point in these embodiments.

Figure 20:
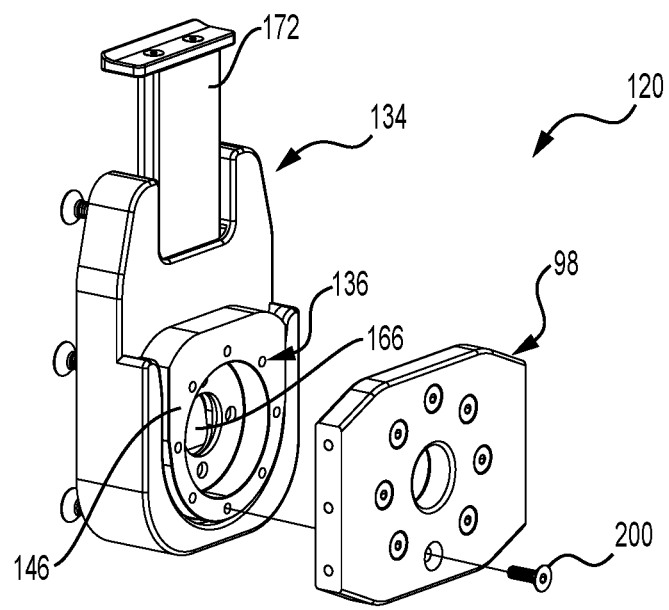
FIG. 20 is a coupling device comprising a base member, a release member, and a top plate, according to certain other embodiments of the present disclosure.

In certain other embodiments (for example as illustrated in FIG. 20), when the base member 134 and the release member 136 are coupled together and in the lock position, the release member 136 is not rotatable within the pocket 162. In this respect, the perimeter 148 of the plate-like body 138 of the release member 136 has an eccentric shape such that the release member 136 is not rotatable in the pocket 162 of the base member 134. The perimeter 148 of the release member 136 may have a shape which is a multi-faceted geometric form. This embodiment of the coupling device 120 may be used when rotation of the equipment 12 is not required. In certain embodiments, the release member 136 further comprises a circular member 206 which is rotatable within the pocket 162 (FIG. 20).

In certain embodiments, the coupling device 120 is further provided with a damping member 208 (FIG. 19) attachable to the back side 154 of the base member 134 and arranged to be positioned between the base member 134 and the surface in use. The damping member 208 is arranged to absorb vibrations and shocks, and/or reduce energy transmission. In certain embodiments, the damping member 208 is made of any suitable material such as elastomeric materials.

Referring back to FIGS. 2 and 6, in certain embodiments, the release member 136 of the coupling device 120 of FIG. 20 is attached the outer side 62 of the back support 14 via a back plate 94. The release member 136 is connectable to the base member 134 (see in FIGS. 3 and 4) and which can be mounted to the patient transportation system 13 (e.g. stretcher, ambulance wall, etc).

In certain embodiments, and with reference to FIGS. 5 and 11, the release member 136 of the coupling device 120 is provided on a lower surface 96 of the bottom plate 44. The corresponding base member 134 to which the release member 136 can be connected can itself be attached to a frame of a stretcher 13.

Certain embodiments of coupling devices and systems which could be used with the present support system 10, are described in U.S. 62/915,806 filed Oct. 16, 2019, U.S. 62/909,408, filed Oct. 2, 2019, U.S. 62/983,075 filed Feb. 28, 2020, and U.S. 63/027,548 filed May 20, 2020, the contents of which are herein incorporated by reference.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be expressly understood that various technical effects mentioned throughout the description above need not be enjoyed in each and every embodiment of the present technology. As such, it is anticipated that in some implementations of the present technology, only some of the above-described technical effects may be enjoyed. While in other implementations of the present technology, none of the above enumerated technical effects may be present, while other technical effects not specifically enumerated above may be enjoyed. It should be expressly understood that the above enumerated technical effects are provided for illustration purposes only, to enable those skilled in the art to better appreciate embodiments of the present technology and by no means are provided to limit the scope of the present technology or of the claims appended herein below.

It is noted that the foregoing has outlined some of the more pertinent non-limiting embodiments. It will be clear to those skilled in the art that modifications to the disclosed non-embodiment(s) can be effected without departing from the spirit and scope thereof. As such, the described non-limiting embodiment(s) ought to be considered to be merely illustrative of some of the more prominent features and applications. Other beneficial results can be realized by applying the non-limiting embodiments in a different manner or modifying them in ways known to those familiar with the art. This includes the mixing and matching of features, elements and/or functions between various non-limiting embodiment(s) is expressly contemplated herein so that one of ordinary skill in the art would appreciate from this disclosure that features, elements and/or functions of one embodiment may be incorporated into another embodiment as skill in the art would appreciate from this disclosure that features, elements and/or functions of one embodiment may be incorporated into another embodiment as appropriate, unless described otherwise, above. Although the description is made for particular arrangements and methods, the intent and concept thereof may be suitable and applicable to other arrangements and applications.

What is claimed is:

1. A support system for supporting equipment, the support system comprising:
   a back support;
   a plurality of shelves spaced from one another and extending from the back support, a given shelf of the plurality of shelves arranged to support a given unit of equipment and comprising:
      a connecting mechanism for providing a connected position in which the given unit of equipment is connected to the given shelf such that separation of the given shelf and the given unit of equipment along a first axis is blocked but relative movement along a second axis is possible;
      a locking mechanism for providing a locked position in which relative movement of the given unit of equipment and the given shelf along the second axis is blocked;
      a release mechanism for releasing the locked position to permit the relative movement along the second axis, the release mechanism including an actuator on the given shelf or the given unit of equipment which can be actuated by a user;
      the locking mechanism having a retractable tongue for engagement in a notch, the retractable tongue actuatable between an extended position and a retracted position using the actuator; and
      the release mechanism having:
         an actuator component including the actuator; and
         a tongue component including the retractable tongue, wherein the actuator component and the tongue component are connected by a pin and groove assembly such that actuating the actuator causes retraction of the tongue.

2. The support system of claim 1, wherein the back support and the given shelf are positioned at substantially 90 degrees to one another, and wherein, in use, the back support is arranged to be positioned substantially vertically and the plurality of shelves are arranged to be positioned substantially horizontally, one above each other.

3. The support system of claim 1, wherein the first axis is a vertical direction and the second axis is a horizontal direction.

4. The support system of claim 1, further comprising the given unit of equipment.

5. The support system of claim 1, wherein the connecting mechanism comprises inter-engaging portions to mechanically connect the given unit of equipment and the given shelf in the connected position.

6. The support system of claim 5, wherein the inter-engaging portions comprise a tongue and groove.

7. The support system of claim 1, wherein the retractable tongue is resiliently biased to the extended position.

8. The support system of claim 1, wherein the retractable tongue is provided on the given shelf and the notch is defined in a side wall of the given unit of equipment.

9. The support system of claim 1, further comprising a top plate extending from an upper end of the back support and a bottom plate extending from a lower end of the back support.

10. The support system of claim 9, wherein the top plate has an opening formed therein to define a handle.

11. The support system of claim 9, further comprising at least one foot extending from the bottom plate.

12. The support system of claim 1, further comprising a mounting mechanism for mounting the support system to a support surface.

13. The support system of claim 1, further comprising a release member of a coupling device, the release member comprising a plate-like body with a first side, the first side defining a planar contact face, and a second side having a collar extending therefrom, the collar positioned inwardly of a perimeter of the release member to define a flange portion, wherein the release member is connected to one or more of: an outer side of the back support, a lower end of the support system, and an upper end of the support system.

14. The support system of claim 13, further comprising a base member of the coupling device, the base member and the release member being releasably connectable together in a coupled position, the base member being connectable to a support surface and having:
   a front face including a planar contact portion for contacting the contact face of the release member;
   a shoulder extending around a portion of a periphery of the planar contact portion to define a pocket for receiving the release member, the shoulder engageable with a portion of the flange portion of the release member when the release member is positioned on the base member;
   an open access end through which the release member can be slidingly inserted and removed from the pocket;
   a stop member positioned in a recess within the planar contact portion and moveable by a resilient lock mechanism and an actuator between a lock position in which at least a portion of the stop member extends from the recess and abuts an edge of an opening defined in the contact face of the release member in the coupled position, and a release position in which the stop member is retracted into the recess;
   the actuator having a neutral position and a deployed position, wherein when the actuator is in the neutral position, the stop member is resiliently biased towards the lock position.

15. A support system for supporting equipment, the support system comprising:
   a back support;
   a plurality of shelves spaced from one another and extending from the back support, a given shelf of the plurality of shelves arranged to support a given unit of equipment and comprising:
      a connecting mechanism for providing a connected position in which the given unit of equipment is connected to the given shelf such that separation of the given shelf and the given unit of equipment along a first axis is blocked but relative movement along a second axis is possible;
      a locking mechanism for providing a locked position in which relative movement of the given unit of equipment and the given shelf along the second axis is blocked; and
      a release mechanism for releasing the locked position to permit the relative movement along the second axis, the release mechanism including an actuator on the given shelf or the given unit of equipment which can be actuated by a user; and
   a release member of a coupling device, the release member comprising a plate-like body with a first side and a second side, the first side defining a planar contact face, and the second side having a collar extending therefrom, the collar positioned inwardly of a perimeter of the release member to define a flange portion, wherein the release member is connected to an outer side of the back support, a lower end of the support system, or an upper end of the support system.

16. The support system of claim 15, further comprising a base member of the coupling device, the base member and the release member being releasably connectable together in a coupled position, the base member being connectable to a support surface and having:
   a front face including a planar contact portion for contacting the contact face of the release member;
   a shoulder extending around a portion of a periphery of the planar contact portion to define a pocket for receiving the release member, the shoulder engageable with a portion of the flange portion of the release member when the release member is positioned on the base member;
   an open access end through which the release member can be slidingly inserted and removed from the pocket;
   a stop member positioned in a recess within the planar contact portion and moveable by a resilient lock mechanism and an actuator between a lock position in which at least a portion of the stop member extends from the recess and abuts an edge of an opening defined in the contact face of the release member in the coupled position, and a release position in which the stop member is retracted into the recess;
   the actuator having a neutral position and a deployed position, wherein when the actuator is in the neutral position, the stop member is resiliently biased towards the lock position.

17. The support system of claim 15, wherein the back support and the given shelf are positioned at substantially 90 degrees to one another, and wherein, in use, the back support is arranged to be positioned substantially vertically and the plurality of shelves are arranged to be positioned substantially horizontally, one above each other.

18. The support system of claim 15, wherein the connecting mechanism comprises inter-engaging portions to mechanically connect the given unit of equipment and the given shelf in the connected position.

19. The support system of claim 18, wherein the inter-engaging portions comprise a tongue and groove.

20. The support system of claim 15, further comprising a top plate extending from an upper end of the back support and a bottom plate extending from a lower end of the back support.

\* \* \* \* \*